US010456274B2

(12) United States Patent
Murphy et al.

(10) Patent No.: US 10,456,274 B2
(45) Date of Patent: *Oct. 29, 2019

(54) METHOD AND APPARATUS FOR PERFORMING ANTERIOR HIP SURGERY

(71) Applicants: Stephen B. Murphy, Winchester, MA (US); William S. Murphy, Winchester, MA (US)

(72) Inventors: Stephen B. Murphy, Winchester, MA (US); William S. Murphy, Winchester, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/995,432

(22) Filed: Jun. 1, 2018

(65) Prior Publication Data

US 2018/0280158 A1    Oct. 4, 2018

Related U.S. Application Data

(63) Continuation of application No. 14/294,702, filed on Jun. 3, 2014, now Pat. No. 10,016,287.

(Continued)

(51) Int. Cl.
*A61F 2/46* (2006.01)
*A61B 17/17* (2006.01)
(Continued)

(52) U.S. Cl.
CPC ........ *A61F 2/4657* (2013.01); *A61B 17/1746* (2013.01); *A61B 34/10* (2016.02); *A61B 34/25* (2016.02); *A61B 2034/105* (2016.02); *A61B 2034/207* (2016.02); *A61B 2034/2055* (2016.02); *A61F 2/32* (2013.01);
(Continued)

(58) Field of Classification Search
CPC ....... A61F 2/4609; A61F 2/4657; A61B 34/20
See application file for complete search history.

(56) References Cited

U.S. PATENT DOCUMENTS

| 5,141,512 A | 8/1992 | Farmer et al. |
| 7,885,705 B2 | 2/2011 | Murphy |

(Continued)

OTHER PUBLICATIONS

"Notification of Transmittal of the International Search Report and the Written Opinion of the International Searching Authority, or the Declaration," International Filing Date: Jun. 3, 2014, International Application No. PCT/US2014/040645, Applicant: Murphy, Stephen B., dated Oct. 20, 2014, pp. 1-14.

(Continued)

*Primary Examiner* — Andrew Yang
(74) *Attorney, Agent, or Firm* — Cesari and McKenna, LLP

(57) ABSTRACT

An apparatus registers a patient's pelvis during surgery by establishing a patient-specific, supine pelvic reference plane. The apparatus may include an elongated support arm having three legs, at least two of which may be moveable along the arm. The first leg may contact the patient's right anterior superior iliac spines (ASIS), the second leg may contact the left ASIS, and the third leg may contact an anterior aspect of the ischium of the patient's pelvis below the acetabulum of the hip being operated on. The distances between the first leg and the second and third legs may be determined preoperatively so that the legs dock to the desired points. The apparatus may further include a direction indicator configured to point in a desired orientation for inserting an acetabular cup component in the patient's acetabulum.

37 Claims, 19 Drawing Sheets

Related U.S. Application Data

(60) Provisional application No. 61/901,580, filed on Nov. 8, 2013, provisional application No. 61/901,341, filed on Nov. 7, 2013, provisional application No. 61/830,263, filed on Jun. 3, 2013.

(51) Int. Cl.
  *A61B 34/10* (2016.01)
  *A61F 2/32* (2006.01)
  *A61B 34/20* (2016.01)
  *A61B 34/00* (2016.01)

(52) U.S. Cl.
  CPC .......... *A61F 2002/4658* (2013.01); *A61F 2002/4668* (2013.01); *A61F 2002/4687* (2013.01)

(56) References Cited

U.S. PATENT DOCUMENTS

| | | |
|---|---|---|
| 8,267,938 B2 | 9/2012 | Murphy |
| 8,986,309 B1 | 3/2015 | Murphy |
| 2008/0077004 A1 | 3/2008 | Henning |
| 2009/0171370 A1 | 7/2009 | Yoon et al. |
| 2009/0306679 A1 | 12/2009 | Murphy |
| 2012/0190971 A1 | 7/2012 | de Wekker |
| 2013/0018666 A1 | 1/2013 | Murphy et al. |
| 2013/0165941 A1 | 6/2013 | Murphy |
| 2014/0358151 A1 | 12/2014 | Murphy et al. |

OTHER PUBLICATIONS

Murray, D. W., "The Definition and Measurement of Acetabular Orientation," The Journal of Bone and Joint Surgery, British Editorial Society of Bone and Joint Surgery, vol. 75-B, No. 2, Mar. 1993, pp. 228-232.

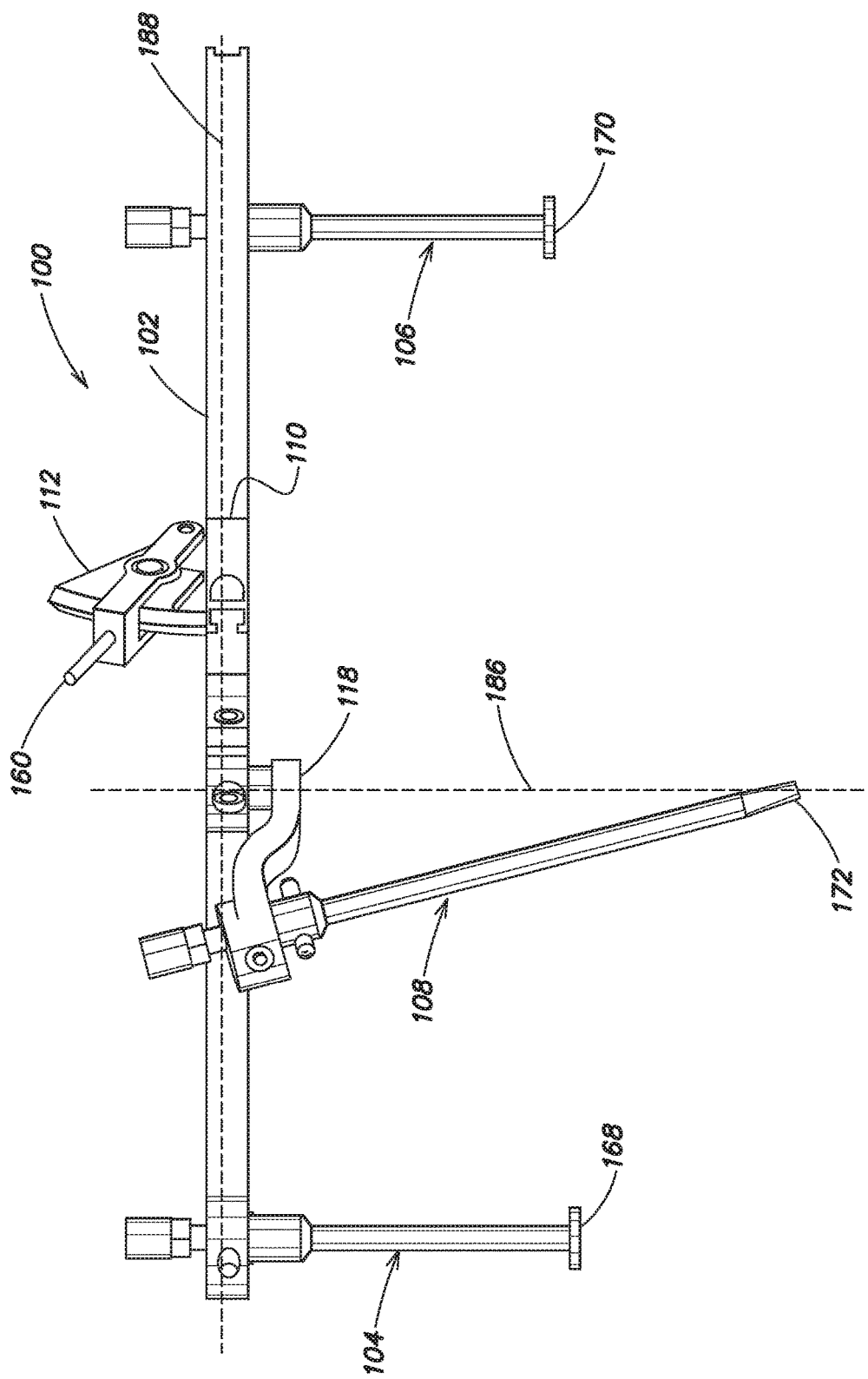

METHOD AND APPARATUS FOR PERFORMING ANTERIOR HIP SURGERY

CROSS-REFERENCE TO RELATED APPLICATIONS

The present application is a continuation of U.S. patent application Ser. No. 14/294,702 which was filed on Jun. 3, 2014, by Stephen B. Murphy and William S. Murphy FOR A METHOD AND APPARATUS FOR PERFORMING ANTERIOR HIP SURGERY, which claims the benefit of U.S. Provisional Patent Application Ser. No. 61/901,580, which was filed on Nov. 8, 2013, by Stephen B. Murphy and William S. Murphy FOR A METHOD AND APPARATUS FOR PERFORMING ANTERIOR HIP SURGERY, U.S. Provisional Patent Application Ser. No. 61/901,341, which was filed on Nov. 7, 2013, by Stephen B. Murphy and William S. Murphy FOR A METHOD AND APPARATUS FOR PERFORMING ANTERIOR HIP SURGERY, and U.S. Provisional Patent Application Ser. No. 61/830,263, which was filed on Jun. 3, 2013, by Stephen B. Murphy and William S. Murphy FOR A METHOD AND APPARATUS FOR PERFORMING ANTERIOR HIP SURGERY, which applications are hereby incorporated by reference in their entireties.

BACKGROUND OF THE INVENTION

Background Information

Surgeons use several different approaches to reach the hip joint when performing hip surgery, such as hip joint replacement (arthroplasty) and resurfacing. In a first approach, known as the posterior (back) approach, the patient is typically placed on his or her side, and the gluteus maximus as well as several small underlying muscles are spread or incised to reach the hip joint. In second and third approaches, known as the anterolateral and direct lateral (side) approaches, the patient is typically placed either on his or her side or back and two large muscles, the gluteus medius and minimus are retracted or partially incised to reach the hip joint. In a fourth approach, known as the anterior (front) approach, the patient is placed on his or her back but instead of incising any large muscles, intervals between muscles are developed and these muscles are separated to reach the hip joint.

U.S. Pat. No. 8,267,938 (the '938 patent) for a Method and Apparatus for Determining Acetabular Component Positioning issued Sep. 18, 2012 to Stephen B. Murphy describes a method and apparatus for determining acetabular cup component positioning, particularly for use in connection with hip arthroplasty and hip resurfacing. The method establishes a coordinate reference frame for the ipsilateral hip, and an apparatus is disclosed that rapidly and reliably establishes the desired coordinate reference frame. A preferred form of the apparatus disclosed in the '938 patent is shown in FIG. 4 from that patent, and comprises a mechanical, manually operated stereotactic instrument in the form of a tripod having a pair of extensible arms extending from a common hub about which the arms can be rotated. First and second legs or cannulas extend from the ends of respective arms remote from the hub and in a manner generally perpendicular to the plane formed by the arms. A third leg or cannula extends from the hub, also generally perpendicular to that plane. The tips of the legs remote from the plane are then positioned by the surgeon or by the instrument itself.

One of the tips may be placed at the root of the ischium, a short distance (e.g., 20 millimeters or so) above the infracotyloid notch. This establishes a "basepoint" or anchor point for proper docking of the instrument to the hip. A second tip may be placed by the surgeon on the lateral side of the iliac wing, adjacent to the anterior superior iliac spine. The third tip then lands on the surface of the lateral ilium, anterior to the sciatic notch. The precise location at which the third tip lands on the ilium is determined by the settings of the instrument. In particular, the landing point is determined by the settings on the extensions of the arms and/or the angles between them. The tips of the three legs, when so positioned, establish a plane and coordinate system, and provide a reference frame with respect to which the orientation of the hip may be referenced.

As described in the '938 patent, an alignment guide in the form of a rod may be affixed to the instrument, and it may be at a defined orientation with respect to the instrument. This defined orientation may be used to define the orientation at which an acetabular cup is to be inserted into the acetabulum by the surgeon. The insertion may be accomplished with the aid of a cup inserter. The cup inserter has a first end onto which an acetabular cup is removably fitted. The cup inserter also includes a handle at the other end, which can be used by the surgeon to position the cup and apply force to seat the cup when it is placed in the desired orientation in the acetabulum. At least a portion of the cup inserter, typically the handle, has a straight segment which can be aligned with the alignment guide by visual inspection.

The apparatus disclosed in the '938 patent is successfully used during hip surgery when using the posterior, lateral, and anterolateral approaches to reach the hip joint.

SUMMARY OF THE INVENTION

Briefly, the present invention relates to a method and apparatus using the anterior approach to perform hip surgery, such as total hip replacement (THR) and hip resurfacing. The apparatus is configured to register the patient's pelvis during surgery by establishing a patient-specific, supine pelvic reference plane and coordinate system. The apparatus includes an elongated support arm sized to extend over the patient's pelvis between the patient's left and right anterior superior iliac spines (ASISs). A first leg may be attached to the elongated support arm. The first leg may have a tip configured to contact the right ASIS. Second and third legs may be slidably attached to the elongated support arm relative to the first leg. The distances between the first leg and the second and third legs may be determined preoperatively so that, when the second and third legs, are set to these predetermined distances along the elongated support arm, a tip of the second leg contacts the left ASIS, and a tip of the third leg contacts an anterior aspect of the ischium of the patient's pelvis below the acetabulum of the hip being operated on. The apparatus may further include a direction indicator that is pivotally adjustable about two planes. A first plane may correspond to a nominal plane defined by an upper surface of the elongated support arm, and a second plane may be perpendicular to the first plane.

The relationship between the patient-specific, supine pelvic reference plane and/or coordinate system and a second plane and/or coordinate system, such as the anterior pelvic plane (the "AP plane") and/or coordinate system may be known. A preferred or desired orientation for an acetabular cup may be determined, for example in terms of the AP plane and/or coordinate system. This preferred and/or desired cup orientation may be translated into the patient-specific, supine pelvic reference plane and/or coordinate system. In an embodiment, the direction indicator is adjusted to point in this preferred or desired orientation for inserting the acetabular cup in the patient's acetabulum. An operating surgeon may access the patient's hip joint using the anterior approach or the anterolateral approach (e.g., with the patient in the supine position), and may dock the apparatus to the patient, thereby registering the patient's pelvis and establishing the patient-specific, supine pelvic reference plane and/or coordinate system. During the procedure, the surgeon may utilize the direction indicator as a guide to insert the acetabular cup component in the preferred or desired orientation.

The apparatus may be used to register the patient's pelvis in three-dimensional (3D) space during the surgical procedure. For example, with the instrument docked to the patient, an object designed to track position can be affixed to the bone and 3 or more discrete points on the apparatus can be input to the tracking system and used to determine the relative positions of the apparatus coordinate system, the tracker coordinate system, and any other coordinate system such as the anterior pelvic plane coordinate system. The tracking system could be any method of tracking including optical, electromagnetic, inertial, or ultrasonic for example. The apparatus may then be removed from the patient, and the tracking system may be used to perform any relevant navigational function including tracking the location and orientation of the acetabular cup component during implantation. The tracking system could also be used to track other instruments such as bone preparation instruments or to track changes in leg length, offset, or anterior-posterior position.

BRIEF DESCRIPTION OF THE DRAWINGS

The invention description below refers to the accompanying drawings, of which:

FIG. 4 is a front elevation view of the surgical instrument of FIG. 1;

DETAILED DESCRIPTION OF ILLUSTRATIVE EMBODIMENTS

Instrument

Figure 1:
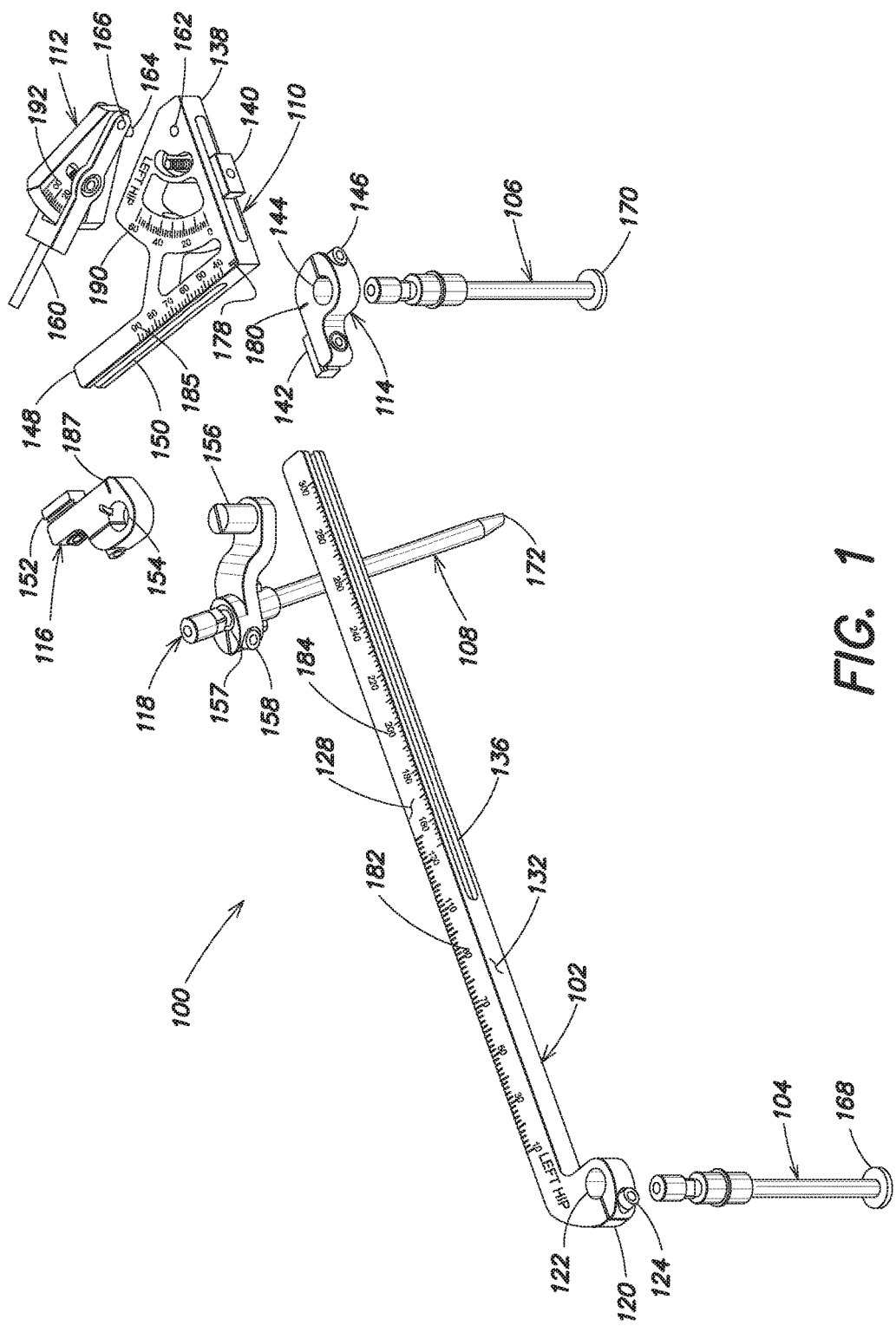
FIG. 1 is an exploded view of a surgical instrument in accordance with an embodiment of the disclosure.
Figure 2:
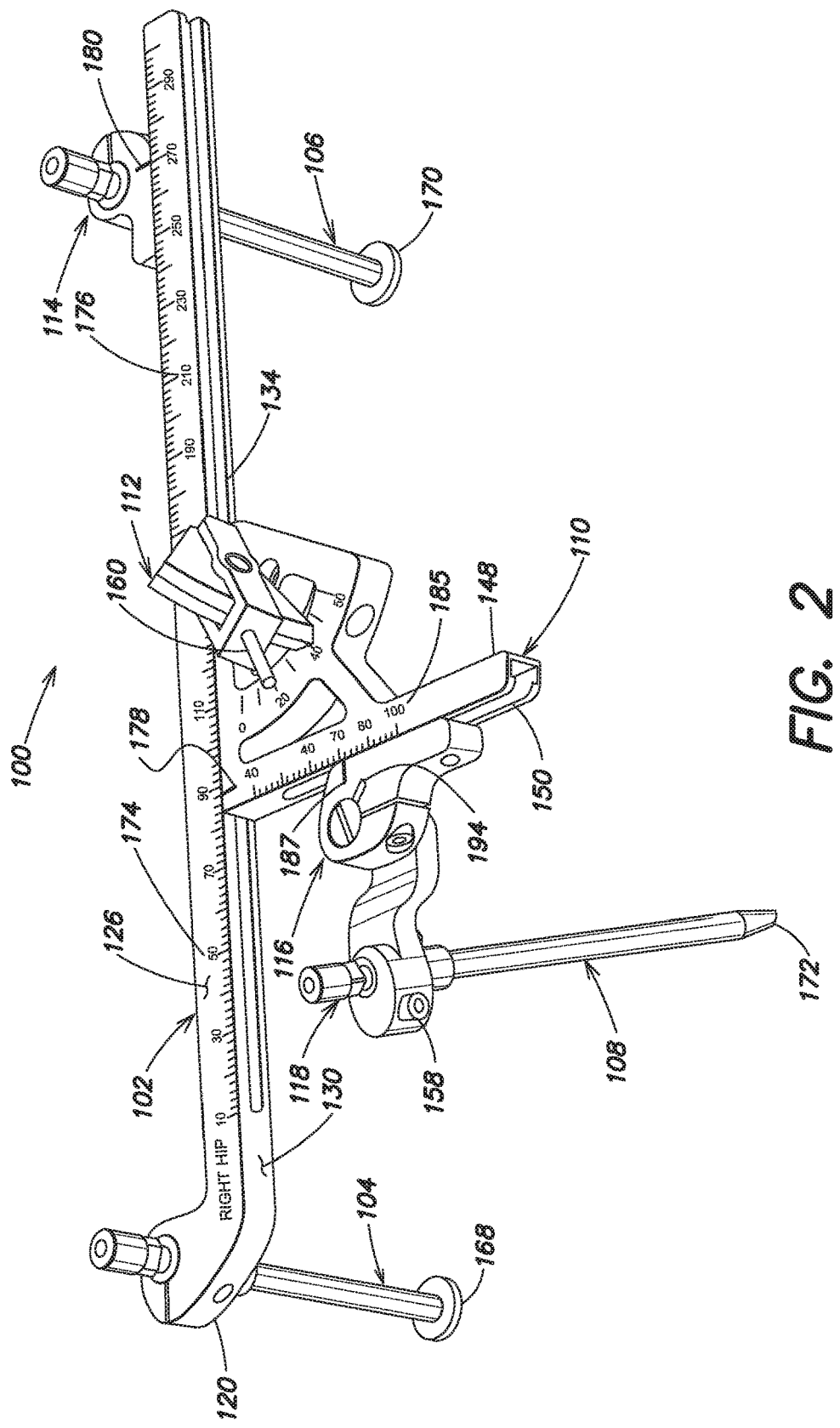
FIG. 2 is a perspective view of the surgical instrument of FIG. 1 as viewed from the top.
Figure 3:
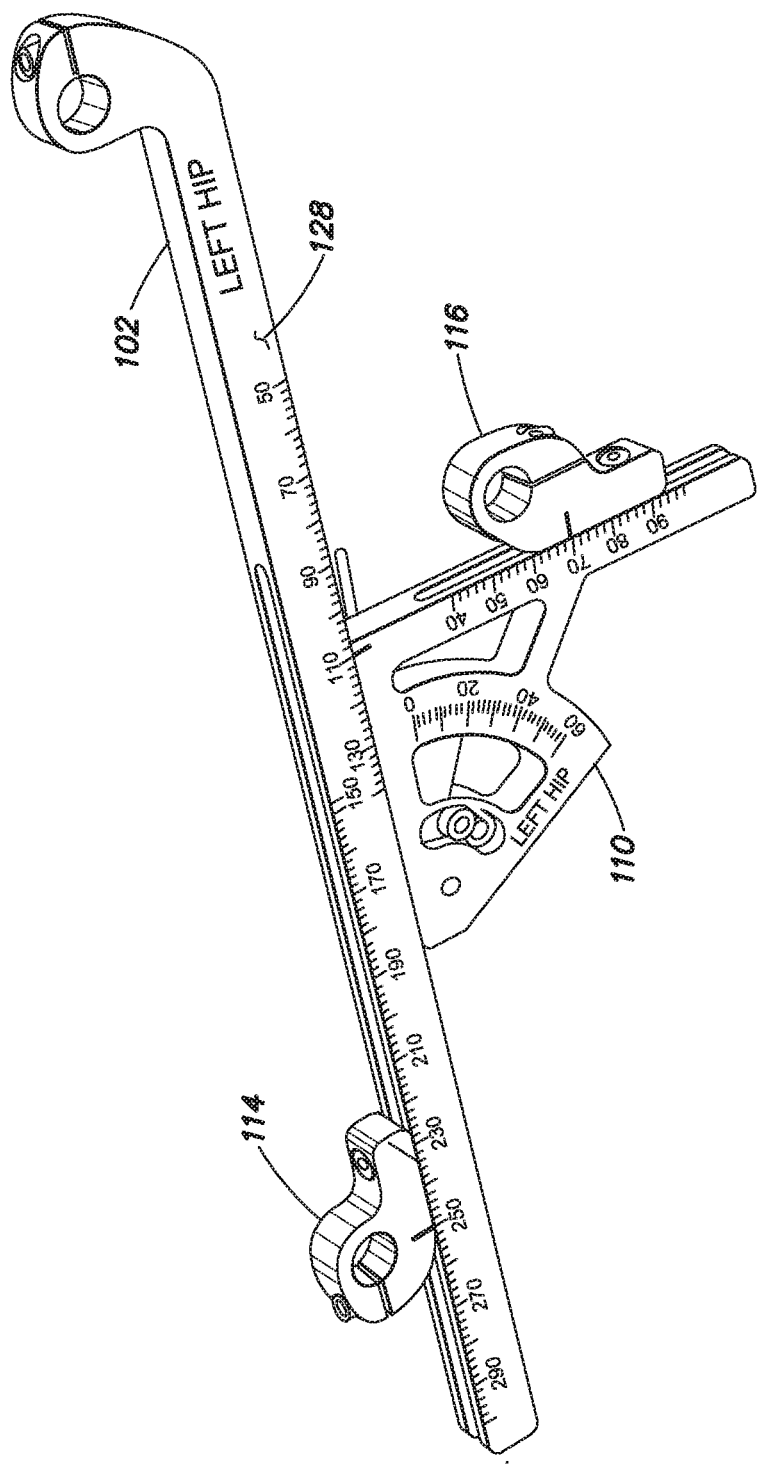
FIG. 3 is a partial, perspective view of the surgical instrument of FIG. 1 as viewed from the bottom.

FIG. 1 is an exploded view of a surgical instrument 100 for use in performing anterior hip surgery in accordance with an embodiment of the present invention. FIG. 2 is a perspective, assembled view of the surgical instrument 100 from as viewed from the top. FIG. 3 is a partial, perspective view of the surgical instrument 100 as viewed from the bottom. FIG. 4 is a front elevation view of the surgical instrument 100.

The surgical instrument 100 may register the location and the orientation of at least a portion of a patient, such as the patient's pelvis, during surgery on the patient, such as total hip replacement (THR) surgery or hip resurfacing, and the instrument 100 may be referred to as a hip registration instrument. With the patient's pelvis registered in space in the operating room, an operating surgeon can install one or more prosthetic components in desired locations and orientations relative to the patient's pelvis.

In an embodiment, the hip registration instrument 100 is a mechanical instrument formed from a plurality of components. In particular, the instrument 100 may include an elongated support arm 102, first, second and third legs 104, 106, and 108, a guide support frame 110, an adjustable guide 112, a direction indicator 160, a first moveable leg brace 114, and a second moveable leg brace 116. In an embodiment, the instrument 100 may also include an offset adapter 118 for use with the third leg 108.

The elongated support arm 102 may include a first end 120. Disposed at the first end 120 may be an opening 122 configured to receive a portion of the first leg 104. The first end 120 may be formed as a clamp having a set screw 124 that may be tightened once the first leg 104 in inserted into the opening 122 so as to secure the first leg 104 to the elongated support arm 102.

In an embodiment, the elongated support arm 102 may have a generally rectangular cross-section, and may include a top surface 126, a bottom surface 128, a front side 130, and a back side 132. A first track 134 may be formed along at least a portion of the front side 130, and a second track 136 may be formed along at least a portion of the back side 132. The first and second tracks 134 and 136 may be recessed tracks, such as slots or grooves.

The guide support frame 110 may include a first edge 138 configured to slidably mount the guide support frame 110 to the front side 130 of the elongated support arm 102. For example, a T-shaped boss 140 may be secured to the first edge 138, and the boss 140 may be configured to fit within the first track 134, which may also be T-shaped, thereby securing the guide support frame 110 to the elongated support arm 102, while allowing the guide support frame 110 to slide along the front side 130 of the elongated support arm 102.

The first moveable leg brace 114, and thus the second leg 106, may be configured for slidable attachment to the back side 132 of the elongated support arm 102. For example, the first moveable leg brace 114 may include a T-shaped boss 142 configured to fit within the second track 136 on the back side 132 of the elongated support arm 102. The first moveable leg brace 114 also may include an opening 144 configured to receive a portion of the second leg 106. The first moveable leg brace 114, or at least a portion thereof, may be formed as a clamp having a set screw 146 that may be tightened once the second leg 106 in inserted into the opening 144 so as to secure the second leg 106 to the first moveable leg brace 114.

The guide support frame 110 may include a second edge 148 to which the second moveable leg brace 116 may slidably attach. For example, a recessed track 150, which may be a slot or groove, may be formed along at least a portion of the second edge 148. The second moveable leg brace 116 may include a T-shaped boss 152 configured to fit within the track 150, which may also be T-shaped, in the guide support frame 110.

The second moveable leg brace 116 may include an opening 154 for receiving a boss 156 formed on the offset adapter 118. The offset adapter 118 also may include an opening 157 for receiving at least a portion of the third leg 108. The opening 157 may be located at an opposite end from the boss 156, and may be formed as a clamp having a set screw 158 that may be tightened once the third leg 108 in inserted into the opening so as to secure the third leg 108 to the offset adapter 118, which in turn is secured to the second moveable leg brace 116.

The adjustable guide 112 may support the direction indicator 160, which may be in the form of a rod, that can be pivoted in two planes. The two planes may be orthogonal to each other. For example, the adjustable guide 112 may be configured to pivot relative to the plane defined by the guide support frame 110. For example, the guide support frame 110 may include a pivot point 162 that receives a pivot pin 164 of the adjustable guide 112. In addition, the direction indicator 160 may be configured to pivot relative to the adjustable guide 112 about a pivot point 166. The adjustable guide 112 may be mounted perpendicular to the guide support frame 110.

The first and second legs 104 and 106 may have flat, disk-shaped footings 168 and 170 at their tips. The third leg 108 may have a pointed tip 172.

First and second distance markings 174 and 176 may be included on the top surface 126 of the elongated support arm 102. In addition, aligning lines 178 and 180 may be formed on the guide support frame 110 and the first moveable leg brace 114, respectively. Accordingly, the guide support frame 110 and the first moveable leg brace 114 may be moved to desired locations along the length of the elongated support arm 102. The distance markings 174 and 176 may indicate the distance, e.g., in centimeters, from the first leg 104.

Third and fourth distance markings 182 and 184 may be included on the bottom surface 128 of the elongated support arm 102.

A fifth distance marking 185 may be provided along the second edge 148 of the guide support frame 110 to which the second moveable leg brace 116 is slidably attached. In addition an aligning line 187 may be formed on the second moveable leg brace 116. Accordingly, the second moveable leg brace 116 may be positioned at a known and predetermined position along the side of the guide support frame 110.

Referring to FIG. 4, in an embodiment, the first and second legs 104 and 106 may extend perpendicularly from the elongated support arm 102. In addition, the second moveable leg brace 116, the offset adapter 118 and the third leg 108 may be configured so that the tip 172 of the third leg 108 is positioned directly underneath the opening 154 in the second moveable leg brace 116, as indicated by dashed line 186 passing through the opening 154. Additionally, the second moveable leg brace 116, the offset adapter 118 and the third leg 108 may be configured so that the nominal plane 188 defined by the elongated support arm 102 and the guide support frame 110 is parallel to, and raised above, the plane defined by the tips 168, 170, and 172 of the legs 104, 106, and 108, respectively.

It should be understood that the offset adapter 118 may be configured to position the third leg 108 so that it or some other part of the instrument 100, such as the guide support frame 110, does not interfere with the surgeon's operating field.

In an another embodiment, the offset adapter 118 may be eliminated and the third leg 108 may be secured in the opening 154 of the second moveable leg brace 116 and extend perpendicularly from the elongated support arm 102 like the first and second legs 104 and 106.

While the legs 104, 106, and 108 are shown in FIGS. 1, 2, and 4 as being straight leg elements, it should be understood that other configurations may be used. For example, the third (ischial) leg 108 may include one or more smooth or abrupt angles.

In another embodiment, the legs 104, 106, and 108 may be of unequal length. For example, the third leg 108 may be longer than the first and second legs 104 and 106, which may be the same length.

A first set of angle markings 190 may be formed on a top surface of the guide support frame 110 to specify, e.g., quantify, an in-plane angle position of the adjustable guide 112 and thus of the direction indicator 160, where "in-plane" refers to the nominal plane 188 defined by the elongated support arm 102 and the guide support frame 110. In addition, a second set of angle markings 192 may be formed on the adjustable guide 112 to specify, e.g., quantify, an off-plane angle position of the direction indicator 160.

At least some of the components of the surgical instrument 100 may be formed from surgical grade materials, such as anodized aluminum, stainless steel, etc. In an embodiment, some components are made from stainless steel while others are made from anodized aluminum. The surgical instrument 100 may thus be sterilized and re-used with multiple patients.

In another embodiment, the surgical instrument may be formed from one or more plastic materials, and may be disposed of after a single use.

As described herein, the instrument 100 may be used on either the left or right hip by flipping the instrument over, switching the adjustable guide 112 to the opposite surface, and inserting the legs 104, 106, and 108 from the opposite side.

Procedure

A patient may be diagnosed with a medical condition, such as hip joint failure, that requires surgery, such as total hip replacement (THR) surgery. The hip failure may be on the left hip, the right hip, or on both hips. In preparation for performing the surgery, one or more images, such as Computed Tomography (CT), Magnetic Resonance Imaging (MRI), conventional radiographs (X-rays), or ultrasonic images, may be taken of the patient, or at least of that portion of the patient's anatomy on which the surgery is to be performed, e.g., the pelvis. The one or more digital images may provide three-dimensional (3D) information regarding the surface and/or structure of the patient's pelvis or at least a portion thereof. It should be understood that any diagnostic test or measurement, particularly one that provides dimensional understanding about the specific portion of the patient's anatomy to be operated upon, may be performed and used for patient-specific planning.

In an embodiment, bilateral simultaneous scans, e.g., frontal and lateral digital radiographs, may be taken using, for example, the imaging systems from EOS Imaging S.A. of Paris, France.

It should be understood that other procedures, besides imaging, may be used to obtain a dimensional and/or surface structure understanding of the patient's anatomy. For example, statistical approaches that rely on the patient's sex, height, weight, age, and one or more observable dimensions, may be used.

A surgical planner, such as an experienced surgeon or other person, may utilize planning software to create an electronic surgical plan for the surgery that is to be performed on the patient. For example, the surgical planner may create a plan for inserting one or more prosthetic or surgical components, such as an acetabular cup component, into the patient's hip during THR surgery. The surgical plan may incorporate the use of one or more surgical instruments, including the hip registration instrument 100, to place the acetabular cup component in a desired position and/or orientation within the patient's acetabulum.

The planning software may include a 3D modeling package, which may be operated to create a computer-generated, 3D model of the patient's anatomy, such as the patient's pelvis, based on one or more images. The 3D model may accurately represent the dimensions and surface structure of the patient's pelvis.

Using the planning software, the surgical planner may establish a standard pelvic plane and/or coordinate system, such as the anterior pelvic plane (the "AP plane"), on the 3D model of the patient's pelvis. For example, the 3D modeling package may include a tool that determines the spatial coordinates of points selected on the 3D model, e.g., by the surgical planner operating a pointing device. To define the AP plane coordinate system, the surgical planner may select three points on the surface of the 3D model of the patient's pelvis, such as the left anterior superior iliac spine (ASIS), the right ASIS, and the pubic symphysis. Alternatively, the planning software may be configured to analyze the 3D model and automatically define the AP plane, for example by automatically identifying the three points described above. The 3D modeling package may further include a tool for defining a plane and/or a coordinate system, e.g., on the basis of three selected points.

Figure 5A:
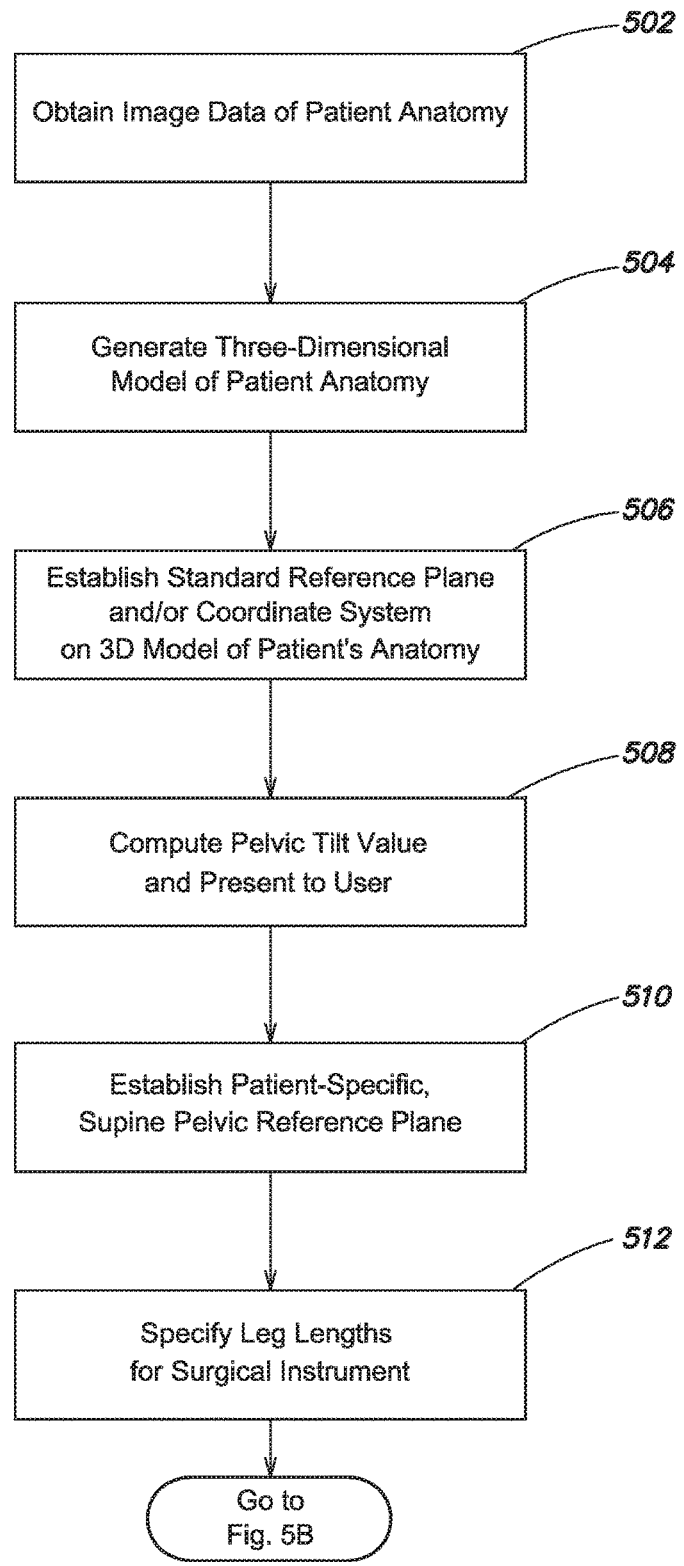
FIGS. 5A-C are partial views of a flow diagram of a method in accordance with an embodiment of the disclosure.
Figure 5B:
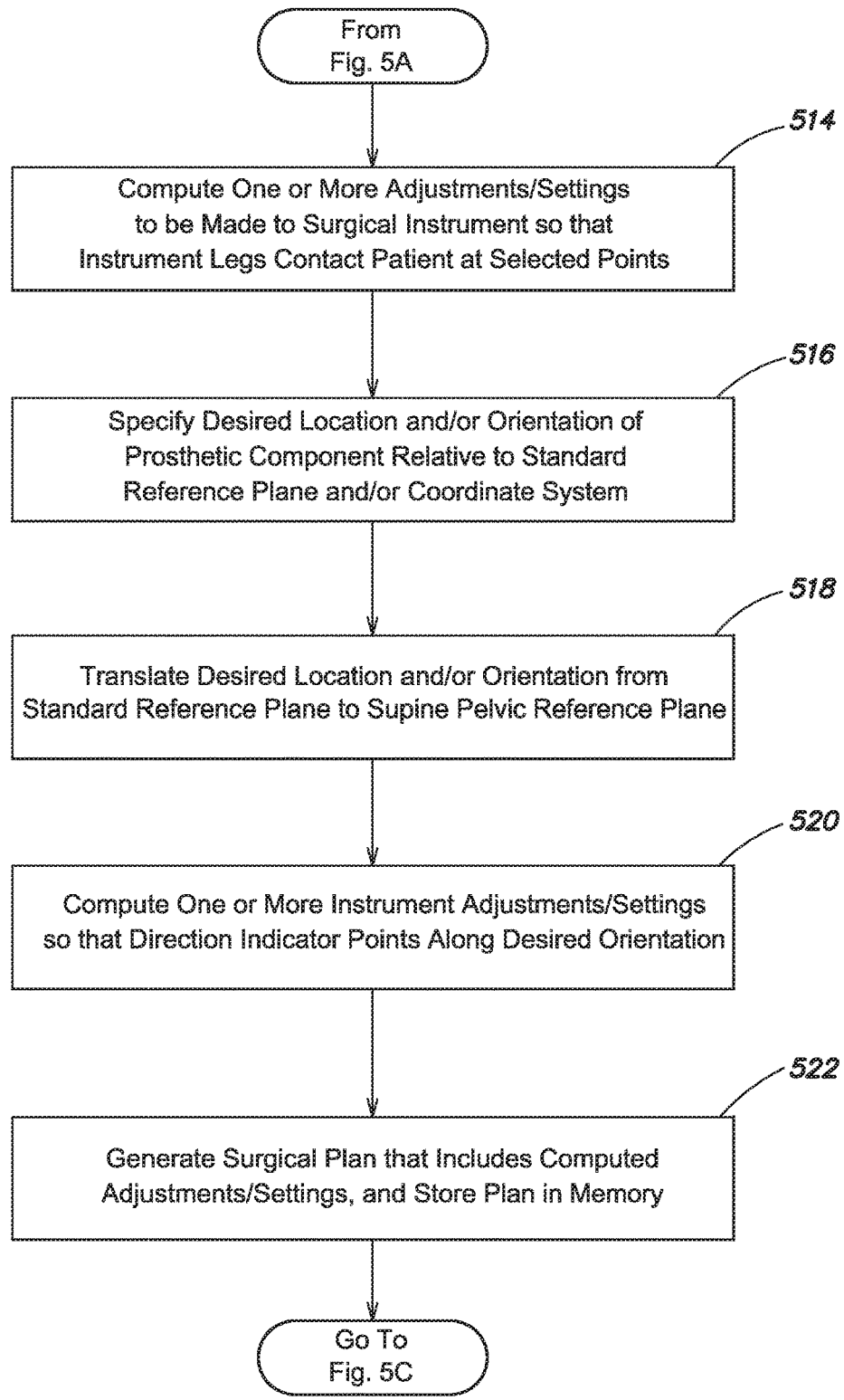
Figure 5C:
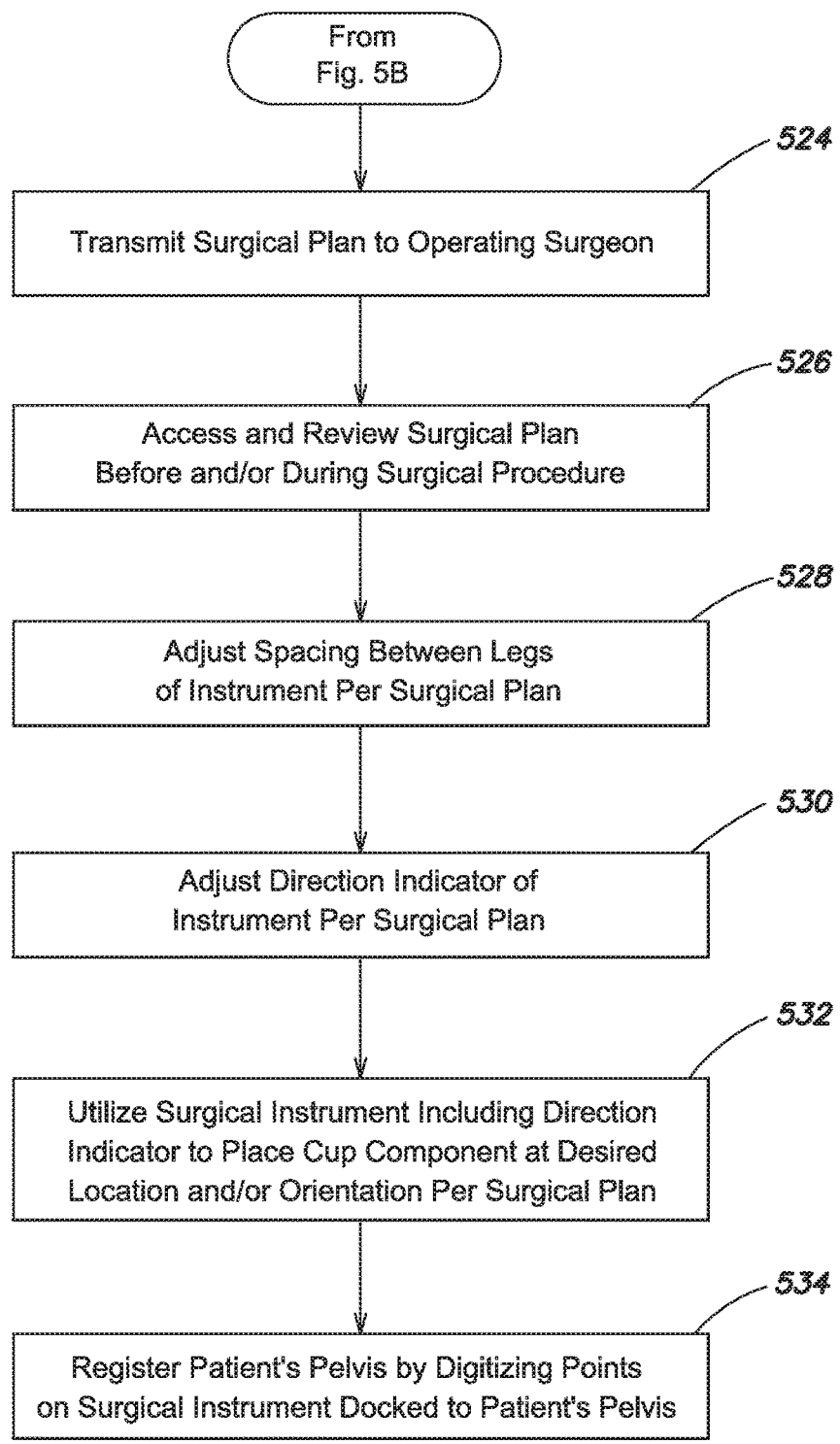

FIGS. 5A-C are partial views of a flow diagram of a procedure in accordance with an embodiment of the disclosure.

Planning Stage

A patient may be diagnosed with a medical condition, such as hip joint failure, that requires surgery, such as total hip replacement (THR) surgery. The hip failure may be on the left hip, the right hip, or on both hips. In preparation for performing the surgery, image data, which may include one or more digital or analog images, such as Computed Tomography (CT) image data, Magnetic Resonance Imaging (MRI) image data, conventional radiographs (X-rays), simultaneous bi-plane radiographic scans, or ultrasonic images, may be taken or obtained of the patient, or at least of that portion of the patient's anatomy on which the surgery is to be performed, e.g., the pelvis, as indicated at block 502. The one or more digital or analog images may provide three-dimensional (3D) information regarding the surface and/or structure of the patient's pelvis or at least a portion thereof.

The obtained image data may include a coordinate system, where a coordinate system for three-dimensional space may be defined by an origin point together with three orthogonal, unit vectors. For example, for CT and MRI image data, a Right, Anterior, Superior (RAS) coordinate system may be defined, which may be fixed relative to the scan table or the scanner and may be equated with the patient's body planes, such as the patient's frontal, median sagittal, and transverse planes.

In an embodiment, bilateral simultaneous scans, e.g., frontal and lateral digital radiographs, may be taken using, for example, the imaging systems from EOS Imaging S.A. of Paris, France.

It should be understood that any diagnostic test or measurement, particularly one that provides dimensional understanding about the specific portion of the patient's anatomy to be operated upon, may be performed and used for patient-specific planning. For example, other procedures, besides imaging, may be used to obtain a dimensional and/or surface structure understanding of the patient's anatomy, such as statistical approaches that rely on the patient's sex, height, weight, age, and one or more observable dimensions.

A surgical planner, such as an experienced surgeon or other person, may utilize a planning system to create an electronic surgical plan for the surgery that is to be performed on the patient. For example, the surgical planner may create a plan for inserting one or more prosthetic or surgical components, such as a prosthetic acetabular cup component, into the patient's hip during THR surgery. The surgical plan may call for the use of one or more surgical instruments, including the hip registration instrument 100, to place the acetabular cup component in a desired position and/or orientation relative to the patient's pelvis.

Figure 13:
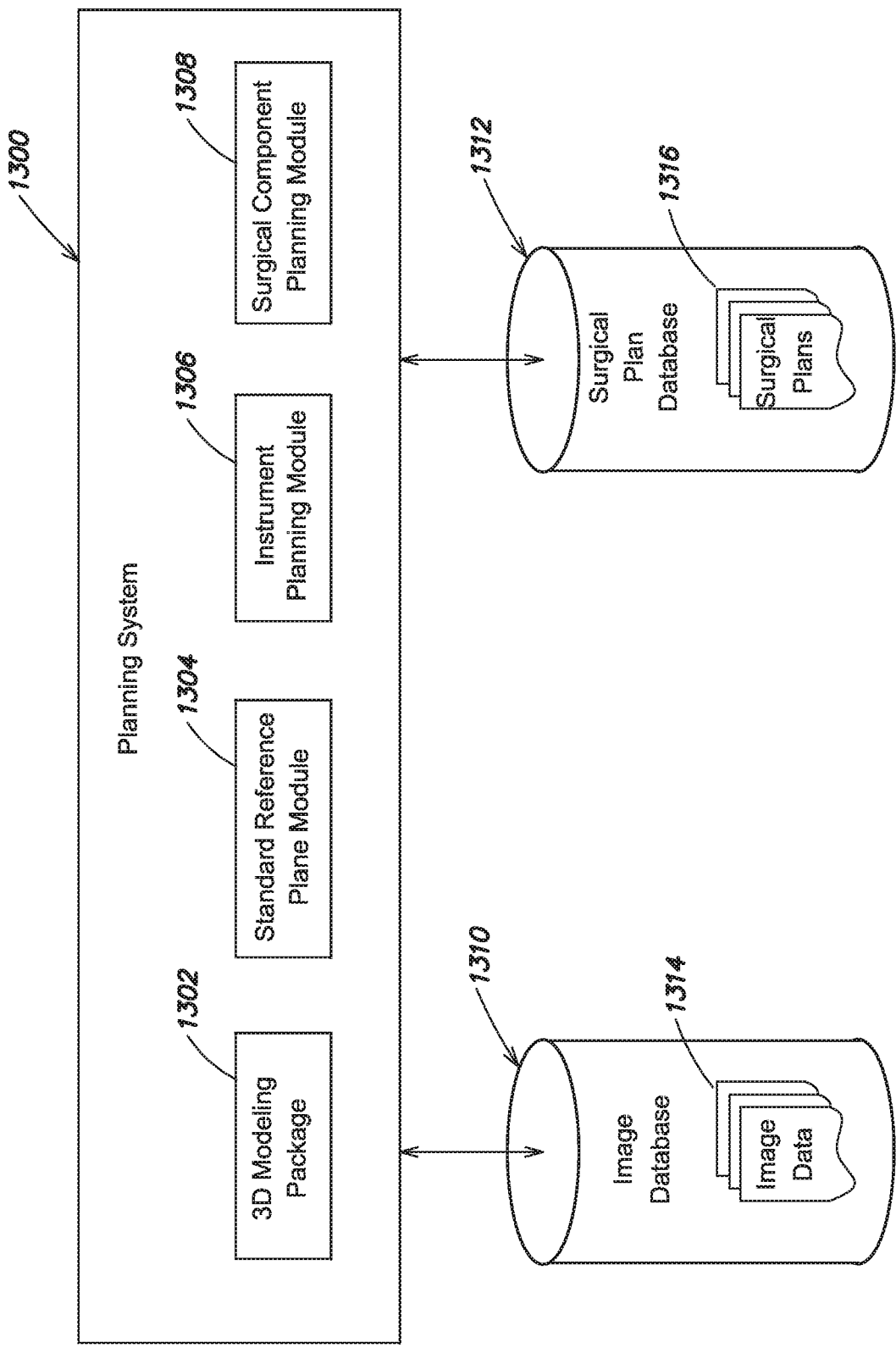
FIG. 13 is a functional, block diagram of a planning system in accordance with an embodiment of the disclosure.

FIG. 13 is a functional, block diagram of a planning system 1300 in accordance with an embodiment of the disclosure. The planning system 1300 may include a plurality of modules or components, such as a three-dimensional (3D) modeling package 1302, a standard reference plane module 1304, an instrument planning module 1306, and a surgical component planning module 1308. The planning system 1300 also may include or have access to one or more databases, such as an image database 1310 and a surgical plan database 1312. A plurality of digital image files designated generally at 1314 may be stored in the image database 1310, and a plurality of surgical plans designated generally at 1316 may be stored in the surgical plan database 1312.

The three-dimensional (3D) modeling package 1302, standard reference plane module 1304, instrument planning module 1306, and surgical component planning module 1308 may each comprise registers and combinational logic configured and arranged to produce sequential logic circuits. In an embodiment, the three-dimensional (3D) modeling package 1302, standard reference plane module 1304, instrument planning module 1306, and surgical component planning module 1308 of the planning system 1300 are or include software modules or libraries containing program instructions pertaining to the methods described herein, that may be stored on computer readable media and executed by one or more processors or processing logic. In alternative embodiments, various combinations of software and hardware, including firmware, may be utilized to implement the present invention.

It should be understood that the planning system 1300 may include other or different components or modules. For example, the planning system 1300 also may include a web hosting facility and a communication facility. In addition, the planning system 1300 may execute on a data processing system, such as a workstation, laptop, tablet, etc. having an operating system that provides display, printing, file system storage, and other computer system utilities.

Nonetheless, it should be understood that other planning systems may be used. For example, another suitable planning system is disclosed in U.S. Pat. Publication No. 2013/0018666 for a Surgical Planning System and Method published Jan. 17, 2013, which publication document is hereby incorporated by reference in its entirety.

The 3D modeling package 1302 may be operated to create a computer-generated, 3D model of the patient's anatomy, such as the patient's pelvis, based on the obtained image data, as indicated at block 504. The computer-generated, 3D model may accurately represent the dimensions and surface structure of the patient's pelvis.

Using the standard reference plan module 1304, the surgical planner may establish a standard pelvic plane coordinate system, such as the anterior pelvic plane (the "AP plane") coordinate system, on the 3D model of the patient's pelvis, as indicated at block 506. For example, the standard reference plan module 1304 may include a tool that determines the spatial coordinates of points selected on the 3D model, e.g., by the surgical planner operating a pointing device, such as a cursor controlled by a mouse, a touchpad, a stylus, or some other input device. To define the AP plane coordinate system, the surgical planner may select three points on the surface of the 3D model of the patient's pelvis, such as the left anterior superior iliac spine (ASIS), the right ASIS, and the pubic symphysis. Alternatively, the standard reference plan module 1304 may be configured to analyze the 3D model and automatically define the AP plane, for example by automatically identifying the three points described above. The standard reference plan module 1304 may be further configured to define a plane and/or a coordinate system, e.g., on the basis of three selected points.

Figure 6:
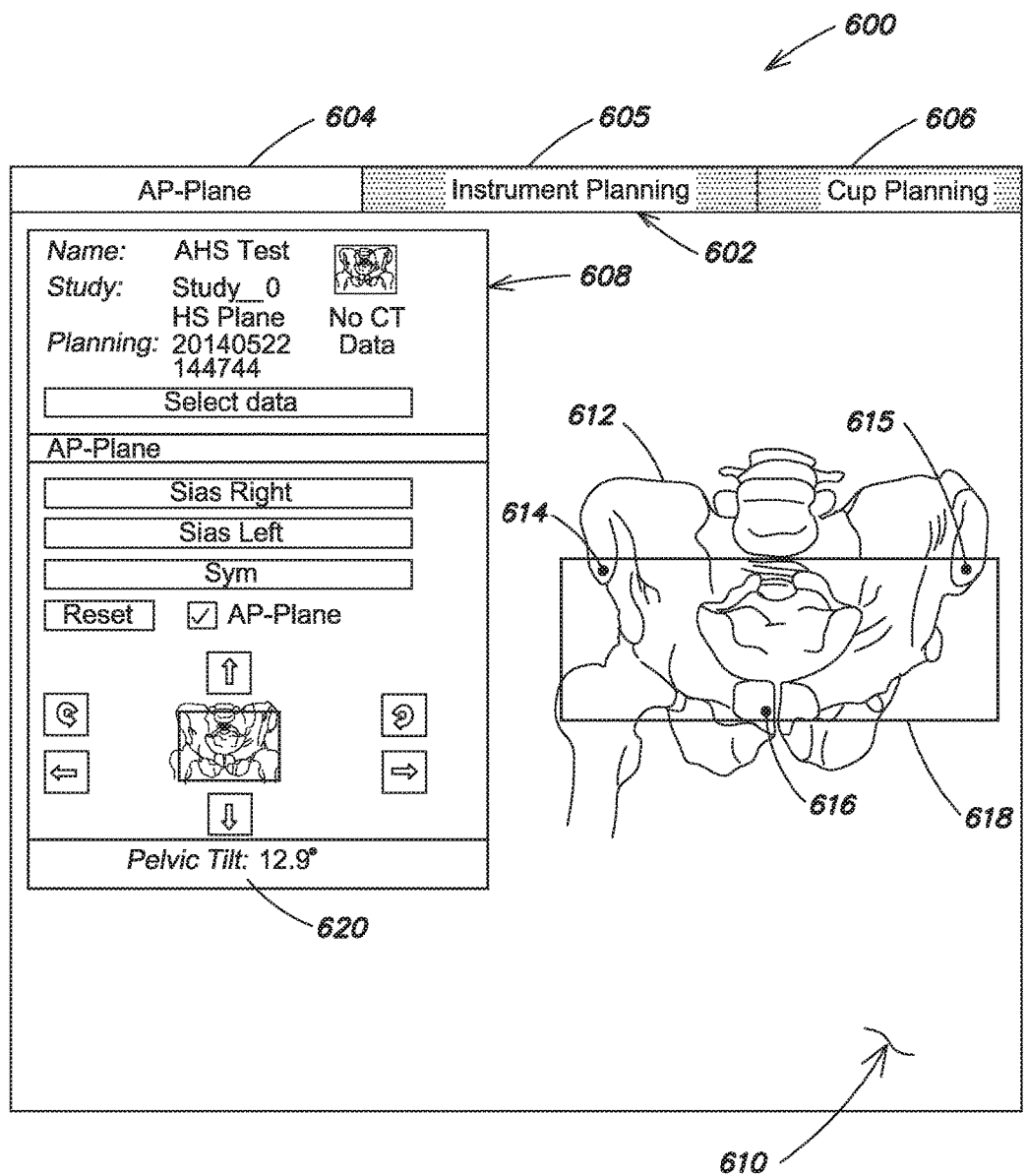
FIG. 6 is a schematic illustration of a first user interface window in accordance with an embodiment of the disclosure.

FIG. 6 is a schematic illustration of a first user interface, which may be a first planning window 600, generated by the surgical planning system 1300, and presented on a display of the data processing device to the surgical planner. The first planning window 600 may include a command ribbon 602 with a plurality of tabs that may be associated with different operation sets or modules of the surgical planning system 1300. The surgical planner may navigate among the different operation sets or modules by selecting a desired tab. Exemplary tabs may include an AP-Plane tab 604, an Instrument Planning tab 605, and a Cup Planning tab 606. The first planning window 600 corresponds to the AP-Plane tab 604.

The first planning window 600 may include an AP plane options selection pane 608 and a model area 610. An image 612 of the 3D model of the patient's pelvis may be presented in the model area 610. Disposed on the surface of the 3D model 612 may be a plurality of graphical elements representing surface points, such as points 614, 615, and 616, which correspond to the right ASIS, the left ASIS, and the pubic symphysis, respectively. An AP plane image 618, which corresponds to the AP plane as defined by the points 614-616, may be presented on the 3D model 612. As noted, the points 614-616 may be selected by the user or determined automatically by the standard reference plane module 1304 of the planning system 1300.

The standard reference plane module 1304 may be further configured to compute a pelvic tilt angle for the patient, and may present the computed value on the first planning window, as indicated at block 508. In particular, the standard reference plane module 1304 may be configured to compute the pelvic tilt angle by determining the angle between the frontal plane as identified by the RAS coordinate system of the CT image data and the AP plane 618 defined by the selection of the three surface points 614-616. The computed pelvic tilt angle, e.g., 12.9°, may be presented on the first planning window 600, for example, in a data field 620 on the options selection pane 608.

With the standard pelvic plane, such as the AP plane 618, and coordinate system defined, the surgical planner may next define a second, patient-specific plane and/or coordinate system for use during the surgical procedure, as indicated at block 510. This patient-specific plane and/or coordinate system may be referred to as the (patient-specific) supine pelvic reference plane and/or coordinate system. In an embodiment, the supine pelvic reference plane and/or coordinate system may be defined by the following three pelvic surface points: a basepoint, which may be at the root of the anterior ischium as it joins the posterior wall of the acetabulum a short distance (e.g., 10 mm or so) medial to the lateral edge of the ischium or 10 mm or so lateral to the medial edge of the ischium, the right ASIS, and the left ASIS. The basepoint may be located on the same side of the pelvis as the hip joint that is being operated on. Suppose, for example, that THR surgery is being performed on the patient's right hip. In this case, the basepoint is also located on the right side of the pelvis. The supine pelvic reference plane and coordinate system does not include the pubic symphysis, and thus the supine pelvic reference plane differs from the AP-plane 618.

It should be understood that other locations within the acetabulum, besides the point described here that is located on the anterior aspect of the ischium, just inferior to the acetabulum may be utilized as the basepoint for the hip registration instrument 100. For example, a central point on the surface of the acetabulum may be selected for the basepoint location.

The patient-specific supine pelvic reference plane may be defined manually, e.g., by the surgical planner, or alternatively, the instrument planning module 1306 of the planning system 1300 may be configured to define the supine pelvic reference plane automatically. To define the supine pelvic reference plane, the surgical planner may select the Instrument Planning tab 605, and the planning system 1300 may be configured to present a second user interface, which may be a second planning window, on a display of the data processing device.

Figure 7:
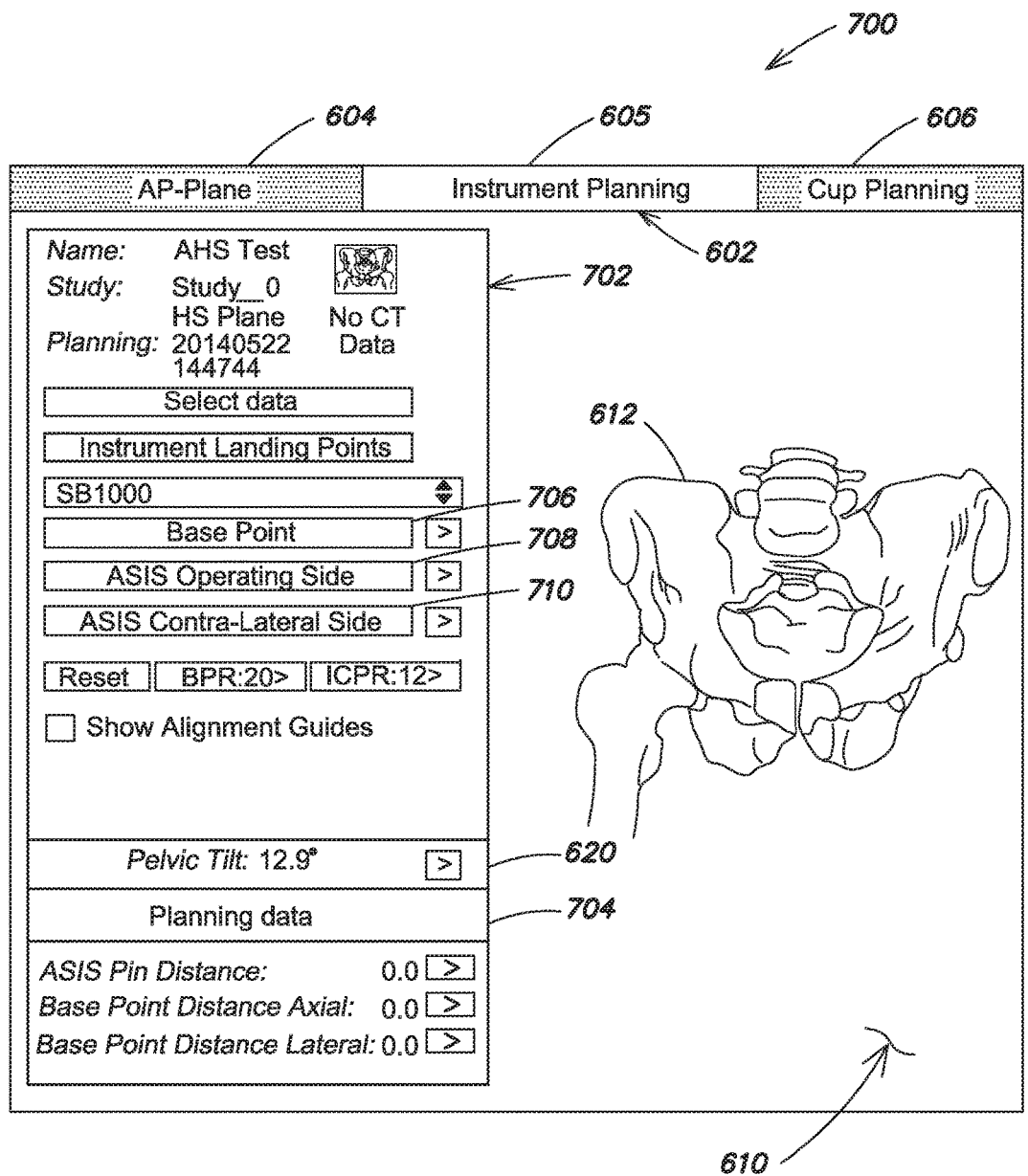
FIG. 7 is a schematic illustration of a second user interface window in accordance with an embodiment of the disclosure.

FIG. 7 is a schematic illustration of a second planning window 700 in accordance with an embodiment of the disclosure. The second planning window 700 may include the command ribbon 602 having tabs 604-606, and the model area 610 having the image 612 of the 3D model of the patient's pelvis. In addition, the second planning window 700 may include an Instrument options selection pane 702 having a planning data area 704. To the extent the hip registration instrument 100 (FIG. 1) is configured to accept legs 104, 106, and 108 having different lengths, the lengths of the legs 104, 106, and 108 that will be used with the hip registration instrument 100 during the surgical procedure being planned may be specified, e.g., by the surgical planner, through the options selection pane 702, as indicated at block 512. For example, the options selection pane 702 may include a first graphical element (labeled Base Point) 706, a second graphical element (labeled ASIS Operating Side) 708, and a third graphical element (labeled ASIS Contra- Lateral Side) 710, which may be data entry fields, drop down menus, etc. The lengths of the legs 104, 106, and 108 that will be used with the hip registration instrument 100 during the surgical procedure being planned may be entered in the data entry fields or drop down menus associated with these graphical elements 706-710.

In an embodiment, selection of the three points on the surface of the pelvis used to define the supine pelvic reference plane may be performed in stages. In a first stage, preliminary locations, which may be points or regions, for the three points may be determined. In a second stage, the preliminary locations may be fine-tuned to arrive at final locations for the three points, where the final locations may represent optimal or near optimal locations for use during the surgical procedure. For example, preliminary points on the right and left anterior superior iliac spines and a preliminary point on the anterior ischium just below the acetabulum may be selected and entered into the planning system 1300. The instrument planning module 1306 may cause discs, cylinders or other graphic elements to appear on the image 612 of the pelvis about the selected points. The initial size, e.g., diameters, of these discs or cylinders may be user-specified, or the instrument planning module 1306 may apply a default size. The images of the discs or symbols may be manipulated by the surgical planner, e.g., moved, narrowed, etc., to fine-tune the location of the points. In an embodiment, the surgical planner may move and/or change the size of the discs or cylinders, e.g., through dragging and expanding/shrinking operations, so that the discs or cylinders define final locations of one or more of the selected points that are specific distances from landmarks or other structures on the pelvis, such as a specific bone edge. The specific distances may be chosen to allow the operating surgeon to locate the final points on the patient's pelvis during the surgical procedure. For example, at least one or more of the specific distances may correspond to a dimension of a tool or guide to be used by the operating surgeon to locate the points on the patient's pelvis during the surgical procedure. It is understood that such fine-tuning procedures may be automated in the software application and may not require specific input by the planner.

Figure 8:
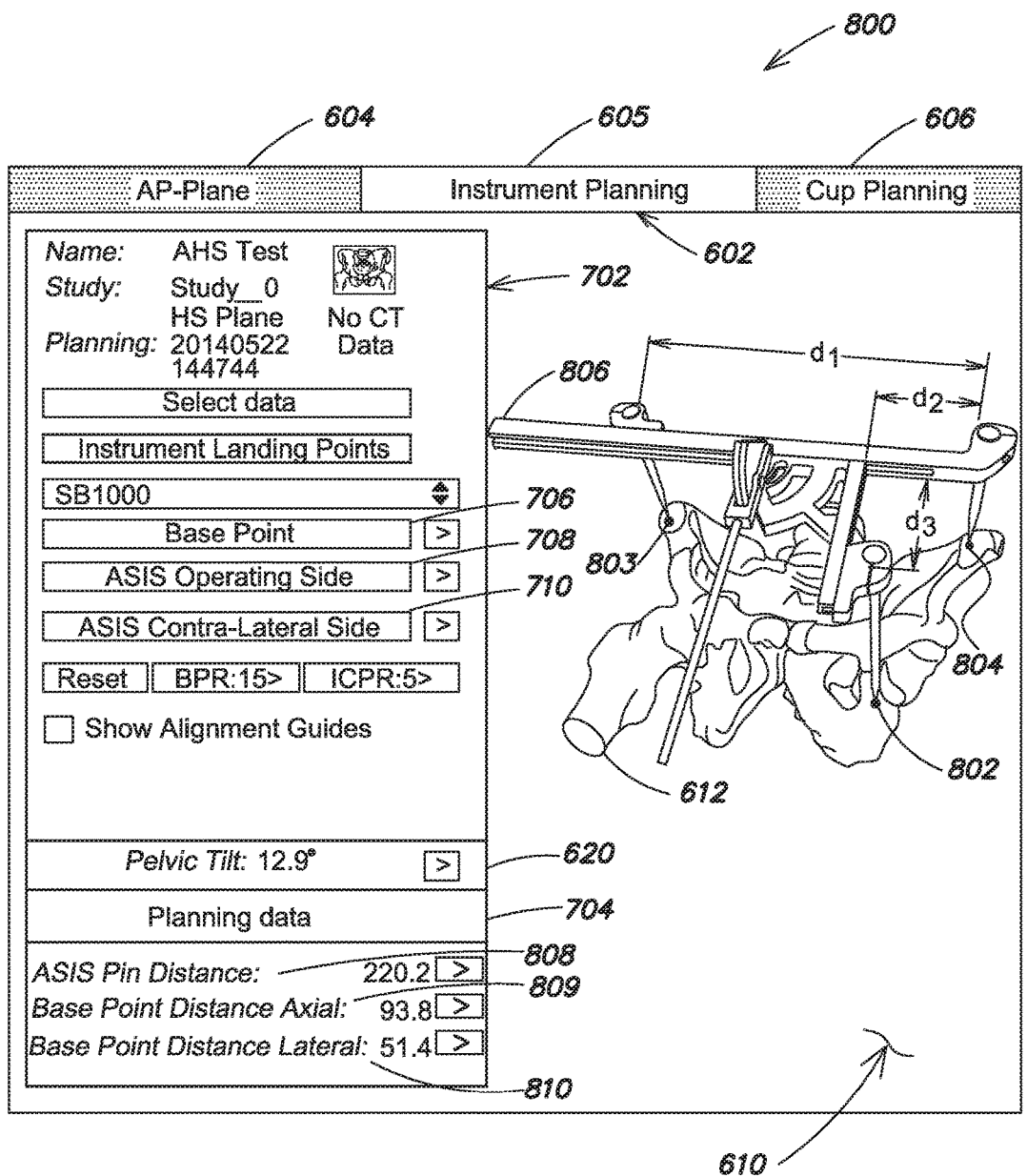
FIG. 8 is a schematic illustration of a third user interface window in accordance with an embodiment of the disclosure.

FIG. 8 is a schematic illustration of a third planning window 800 that may be generated and displayed by the planning system 1300 in accordance with an embodiment of the disclosure. The third planning window 800 may include the command ribbon 602 having tabs 604-606, the model area 610 having the image 612 of the 3D model of the patient's pelvis, and the Instrument options selection pane 702 with the planning data area 704. Graphical elements, such as first, second, and third points 802, 803, and 804, may be included on the image 612 of the pelvis where the points 802-804 represent the three points selected to define the patient-specific supine pelvic reference plane. Specifically, the first point 802 may correspond to the basepoint, the second point 803 may correspond to the right ASIS, and the third point 804 may correspond to the left ASIS. An image 806 of the surgical instrument 100 may also be included in the model area 610, and the instrument image 806 may be shown docked to the pelvis image 612 to illustrate how the physical instrument 100 will dock to the patient during the surgical procedure.

The instrument planning module 1306 may be configured to compute one or more adjustments to the instrument 100 so that the tips of the legs will contact the points selected as defining the supine pelvic reference plane, as indicated at block 514 (FIG. 5B). Specifically, the instrument planning module 1306 may compute a first value that specifies where to place the aligning line 180 of the moveable leg brace 114 relative to the distance marking 176 along the top surface 126 of the elongated support arm 102 so that the tip of the first leg 104 contacts the desired point on the left ASIS and the tip of the second leg 106 contacts the desired point on the right ASIS, as illustrated by the distance marking labeled $d_1$ on FIG. 8. This computed first value, e.g., 220.2 cm, may also be presented in a first entry on the 808 of the planning data area 704 of the options selection pane 702. In addition, the instrument planning module 1306 may compute a second value that specifies where to place the aligning line 178 of the guide support frame 110 relative to the distance marking 174 along the top surface 126 of the elongated support arm 102, and a third value that specifies where to place the aligning line 187 of the second moveable leg brace 116 relative to the distance marking 185 along the second edge of the guide support frame 110. The second and third values, which are represented by the distance markings labeled $d_2$ and $d_3$ on FIG. 8, place the third leg 108 so that its tip contacts the desired basepoint. These computed values, e.g., 51.4 cm and 93.8 cm, may also be presented in second and third entries 809 and 810 of the planning data area 704.

Next, the surgical planner may proceed to the cup planning stage in which he or she chooses a desired location and/or orientation for a prosthetic acetabular cup component, as indicated at block 516. The surgical component planning module 1308 of the planning system 1300 may be configured to assist the surgical planner in choosing an acetabular cup component location and/or orientation.

Figure 9:
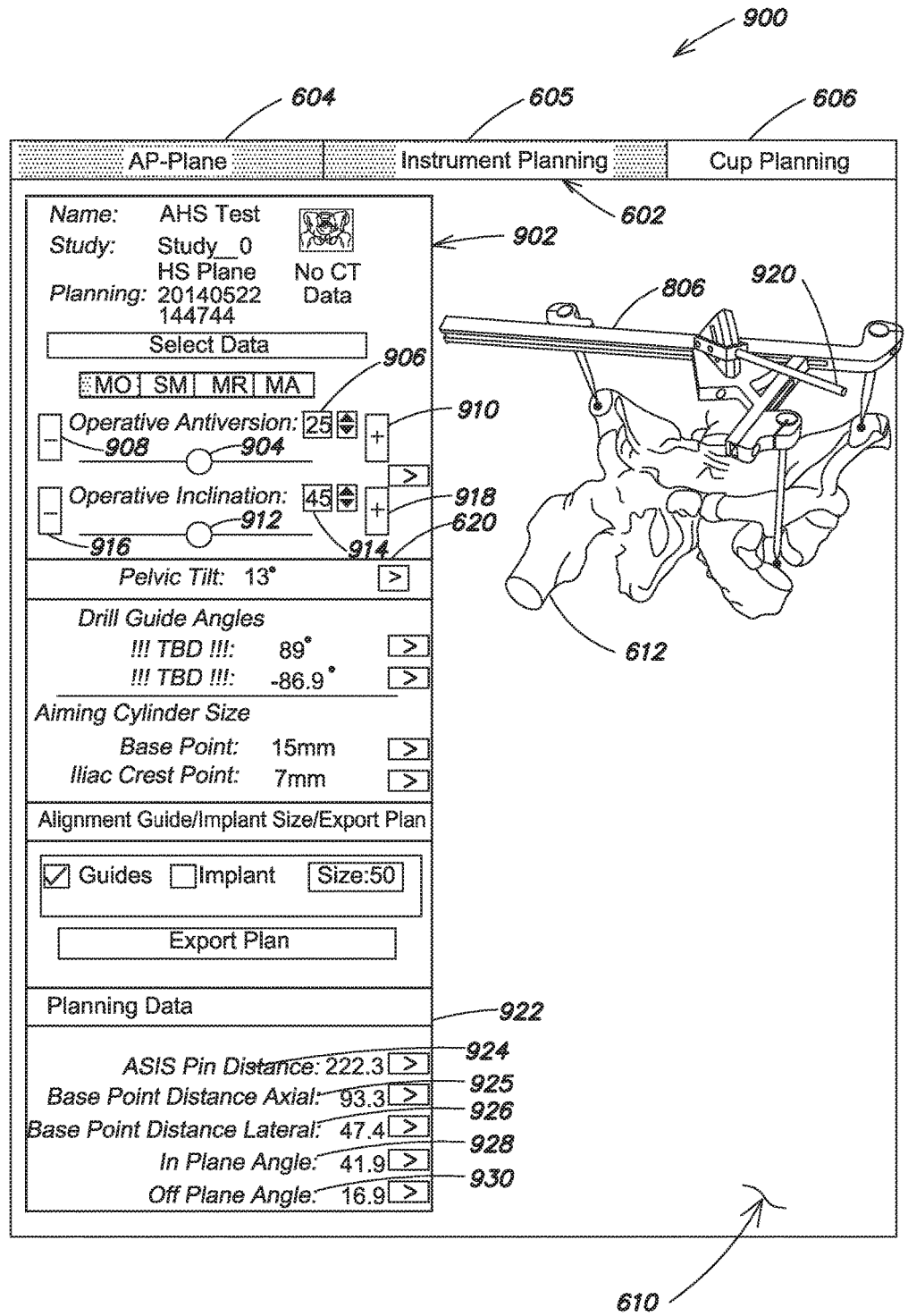
FIG. 9 is a schematic illustration of a fourth user interface window in accordance with an embodiment of the disclosure.

FIG. 9 is a schematic illustration of a fourth planning window 900 that may be generated and displayed by the planning system 1300 in accordance with an embodiment of the disclosure. The fourth planning window 900 may include the command ribbon 602 having tabs 604-606, and the model area 610 having the image 612 of the 3D model of the patient's pelvis and the instrument image 806. The fourth planning window 900 also may include a planning options selection pane 902 that may include the pelvic tilt data field 620.

In an embodiment, the orientation of the prosthetic acetabular cup component may be specified by the surgical planner with reference to the standard pelvic reference plane, e.g., the AP plane 618 (FIG. 6). For example, the selected cup orientation may be defined in terms of operative anteversion and operative inclination of an axis of the cup relative to the AP plane 618 and/or coordinate system. To that end, the planning options selection pane 902 may include one or more interactive graphical elements through which the surgical planner can specify a desired operative anteversion value and an operative inclination value for the cup component. In particular, the planning options selection pane 902 may include a first slider 904, a first data entry box 906, a first minus button 908, and a first plus button 910 any of which may be operated by the surgical planner to specify the desired operative anteversion value. The planning options selection pane 902 also may include a second slider 912, a second data entry box 914, a second minus button 916, and a second plus button 918 any of which may be operated by the surgical planner to specify the desired operative inclination value. By operating these graphical elements, the surgical planner can specify a desired orientation for the acetabular cup component relative to the AP plane 618.

The surgical component planning module 1308 of the planning system 1300 may be further configured to translate the selected cup orientation defined with reference to the AP plane 618 and/or coordinate system into a cup orientation with reference to the patient-specific, supine pelvic reference plane and/or coordinate system, as indicated at block 518. Accordingly, the selected operative anteversion value, e.g., 25°, and the selected operative inclination value, e.g., 45°, which are specified in relation to the AP plane 618 and/or coordinate system may be converted to respective values in the patient-specific supine pelvic reference plane and/or coordinate system, such as inclination and abduction angles relative to the patient-specific supine pelvic reference plane and/or coordinate system.

It should be understood that other cup orientations besides operative anteversion and inclination may be used, such as radiographic anteversion and inclination, and anatomic anteversion and inclination. At least some of these orientations are described in D. W. Murray *The Definition and Measurement of Acetabular Orientation* (© 1993 British Editorial Society of Bone and Joint Surgery), which is hereby incorporated by reference in its entirety. It should also be understood that instead of defining cup orientation relative to standard reference plane and/or coordinate system, such as the AP plane coordinate system, cup orientation may be defined relative to some other reference plane and/or coordinate system, such as the supine pelvic reference plane and/or coordinate system or a functional coordinate system. Such a functional coordinate system may be a coordinate system that lies in the horizontal plane of the pelvis when the patient is lying supine on a table, in the vertical plane of the pelvis when the patient is standing, or in a plane relative to the pelvis as determine by assessment of a combination of dynamic activities such as sitting, standing, lying, bending, and squatting for example. Whatever base coordinate system is chosen for specifying a desired cup orientation, the relationship between that base coordinate system and the patient-specific coordinate system as defined and determined by the instrument 100 would be known and mathematical calculations, including translations and/or transformations, between the two coordinate systems could be calculated by the surgical component planning module 1308 of the planning system 1300.

The instrument image 806 may include a direction indicator 920 that may be shown pointing in the desired cup orientation based on the operative anteversion and inclination values selected by the surgical planner in the planning options selection pane 902. In an embodiment, the surgical component planning module 1308 may be configured to dynamically update the displayed orientation of the direction indicator 920 of the instrument image 806 as the planning surgeon enters new values for desired operative anteversion and inclination. That is, the surgical component planning module 1308 may be configured to dynamically update the displayed position of the direction indicator 920 as the planning surgeon explores different operative anteversion and inclination values. Thus, from the perspective of the planning surgeon, the displayed image of the direction indicator 920 appears to move in real time as new operative anteversion and/or inclination values are entered, e.g., by operating the first and second sliders 904 and 912, or the other graphical elements.

Furthermore, the surgical component planning module 1308 may be configured to incorporate the computed pelvic tilt, e.g., 13°, when determining the orientation of the direction indicator 920 to achieve the desired cup orientation. In further embodiments, knowledge of supine and/or standing pelvic tilt, which may be provided as part of the patient-specific information, can be incorporated in the adjustments to be made to the surgical instrument 100. In addition, other functional data about the patient may be acquired and used in the planning process. For example dynamic assessments, such as deep squatting, sitting, standing, etc., under open MRI, real time fluoroscopic images, or another image or other data gathering technique may be obtained and used in the planning process.

If the legs 104, 106, and 108 of the surgical instrument 100 are of equal length, then the nominal plane 188 of the surgical instrument 100, as defined by the elongated support arm 102 and the guide support frame 110 may be parallel to and spaced-from the patient-specific, supine pelvic reference plane and/or coordinate system defined for the patient by the surface points 802-804. If any one of the legs 104, 106, and 106 have a different length, then the nominal plane of the top surface of the instrument 100 will not be parallel to the patient-specific, supine pelvic reference plane defined by the three points on the surface of the patient's pelvis. Nonetheless, because the lengths of the legs 104, 106, and 106 is known by the planning system 1300, the instrument planning module 1306 may be configured to define this plane in geometric space relative to the patient-specific, supine pelvic reference plane, which is defined by the tips of the instrument's legs. The instrument planning module 1306 may also be configured to translate geometric objects, such as the desired orientation of the acetabular cup component, from the AP plane to the patient-specific supine pelvic reference plane, and from the supine pelvic reference plane to the new plane defined by the nominal plane of the instrument (having different leg lengths). The instrument planning module 1306 may thus be configured to determine the settings for the direction indicator so that it is aligned with the desired orientation as specified relative to the AP plane.

In addition to determining the positions of the moveable second and third legs 106 and 108, the surgical component planning module 1308 may be configured to compute the settings needed to position the direction indicator of the surgical instrument 100 so that, when the instrument 100 is docked to the patient's pelvis, the direction indicator 160 will point along the desired orientation for the cup component, as indicated at block 520. These computed settings may be presented on the planning options selection pane 902. Specifically, the planning options selection pane 902 may also include a planning data area 922 having first, second, and third entries 924-926 for the ASIS pin distance, e.g., 222.3 cm, the axial basepoint distance, e.g., 93.3 cm, and the lateral basepoint distance, e.g., 47.4 cm. The planning data area 922 also may include fourth and fifth entries 928 and 930 for presenting the computed in-plane and off-plane angle settings, e.g., 41.9, and 16.9, respectively, for the guide support frame 110 to position or align the direction indicator 160 with the desired cup orientation.

The surgical component planning module 1308 may generate a surgical plan that includes the computed planning data values, and may store the surgical plan in memory, as indicated at block 522. For example, an electronic surgical plan 1316 may be created and stored in the surgical plan database 1312. Additionally or alternatively, the surgical plan 1316 may be printed.

The surgical plan may thus include the settings necessary to configure the surgical instrument 100 to dock to the patient at the predetermined points, and the settings to cause the direction indicator 160 to point along the desired orientation for the acetabular cup component or along an axis parallel to the desired orientation for the acetabular cup component. Specifically, the surgical plan may include, among other information, the distance setting for the first moveable leg brace 114 along the elongated support arm 102, the distance setting for the guide support frame 110 along the elongated support arm 102, the distance setting for the second moveable leg brace 116 along the side of the guide support frame 116, and the in-plane and off-plane angle settings for the direction indicator 160.

The planning system 1300 may be configured to transmit the electronic surgical plan 1316 created by the surgical planner to the operating surgeon, as indicated at block 524 (FIG. 5C).

Surgical Procedure Stage

The operating surgeon may access the electronic surgical plan before or even during the surgical procedure on the patient, as indicated at block 526. The operating surgeon or an assistant may configure the hip registration instrument 100 based on the values or settings computed by the planning system and specified in the surgical plan. In particular, the spacing between the tips of the legs 104, 106, and 108 may be set to the determined values, as indicated at block 528. That is, the surgeon may slide the first moveable leg brace 114 along the support arm 102 until the marking 180 aligns with the specified distance setting on the support arm 102, e.g., 222.3 cm. The operating surgeon may slide the guide support frame 110 along the support arm 102 until the marking 178 aligns with the specified distance setting on the support arm 102, e.g., 93.3 cm. The operating surgeon may slide the second moveable leg brace 116 along the side of the guide support frame 110 until the marking 187 aligns with the specified distance setting on the guide support frame 110, e.g., 47.4 cm. Once the hip registration instrument 100 has been configured in accordance with the surgical plan, the instrument 100 may be docked, e.g., attached, to the patient, thereby registering the patient's pelvis in space. In other words, with the positions of the tips of the first, second, and third legs 104, 106, and 108 of the instrument 100 properly adjusted per the distances specified in the surgical plan, the instrument 100, when docked to the patient's pelvis, will contact the three points 504, 506, and 602 that were preoperatively determined to define the patient-specific, supine pelvic reference plane and/or coordinate system.

The surgeon also may adjust the direction indicator 160 according to the in-plane and off-plane angles, e.g., 41.9 and 16.9, computed by the planning system and specified in the surgical plan, as indicated at block 530. Stops or locks, such as locking screws, may be provided on the instrument 100 to hold the direction indicator 160 at the preoperatively determined orientation.

In an embodiment, one or more instruments may be used by the surgeon to help the surgeon locate the basepoint at the ischium. For example, a drill guide that hooks onto an edge of the patient's acetabulum may be used to locate the basepoint. A drill may be used with the drill guide to drill a hole at the basepoint for receiving a pin.

Figure 10:
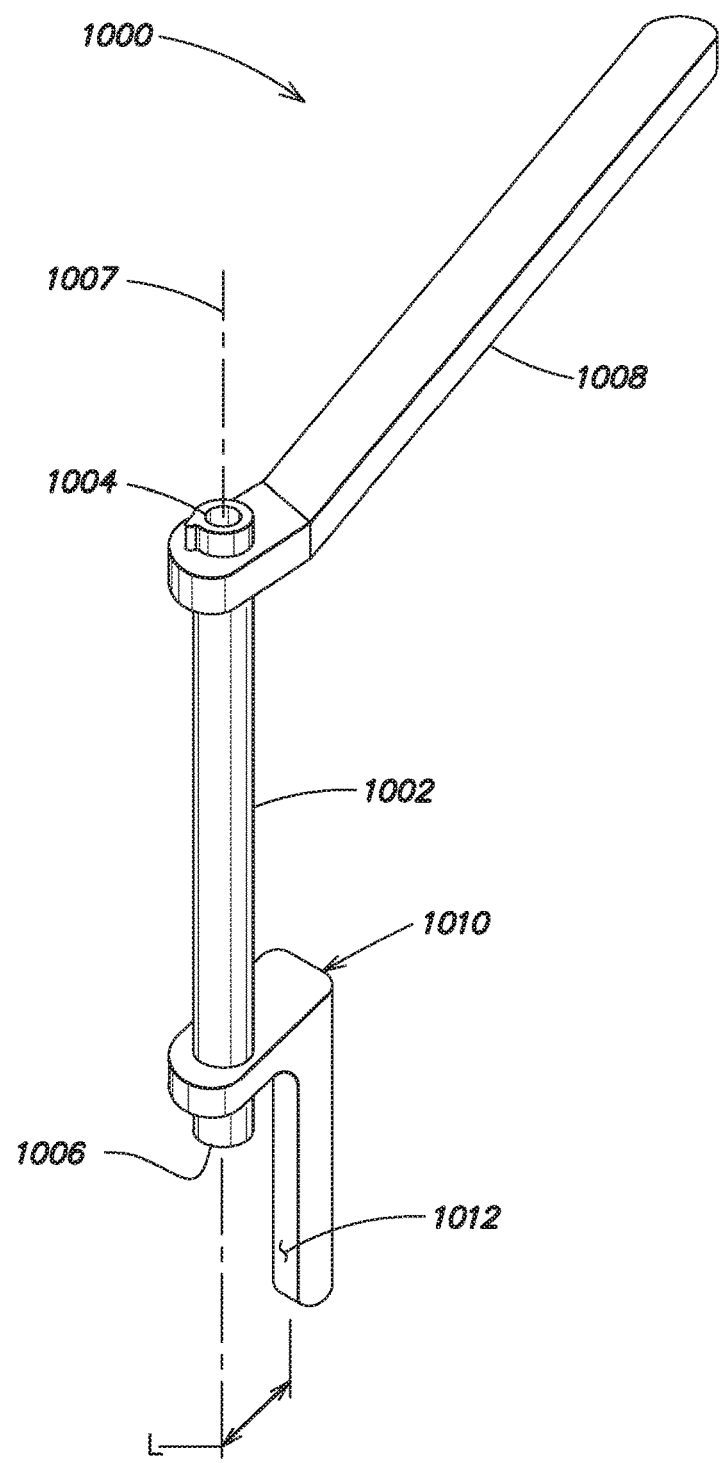
FIG. 10 is a schematic perspective view of a drill guide in accordance with an embodiment of the disclosure.

FIG. 10 is a perspective view of an exemplary drill guide 1000 for use by the operating surgeon for locating the basepoint. The drill guide 1000 may include a cylindrical tube 1002 configured to receive a surgical drill. The cylindrical tube 1002 may include a first opening 1004 for receiving the surgical drill, and a second opening 1006 (opposite the first opening 1004) from which a tip of the surgical drill may be extended. The cylindrical tube 1002 of the drill guide 1000 may define a longitudinal axis 1007. A handle 1008 may be attached to the cylindrical tube 1002, for example proximate to the first opening 1004. The handle 1008 may be configured for grasping by the operating surgeon to hold the drill guide 1000 during use. The drill guide 1000 also may include a finger element 1010 disposed proximate to the second opening 1006. The finger element 1010 may have an engaging surface 1012. The finger element 1010 may be configured so that the engaging surface 1012 is a particular distance, labeled L, from the longitudinal axis 1007. Accordingly, when a surgical drill is passed through the cylindrical tube 1002, the surgical drill will form a hole that is spaced the particular distance L from the engaging surface 1012 of the finger element 1010.

Figure 17:
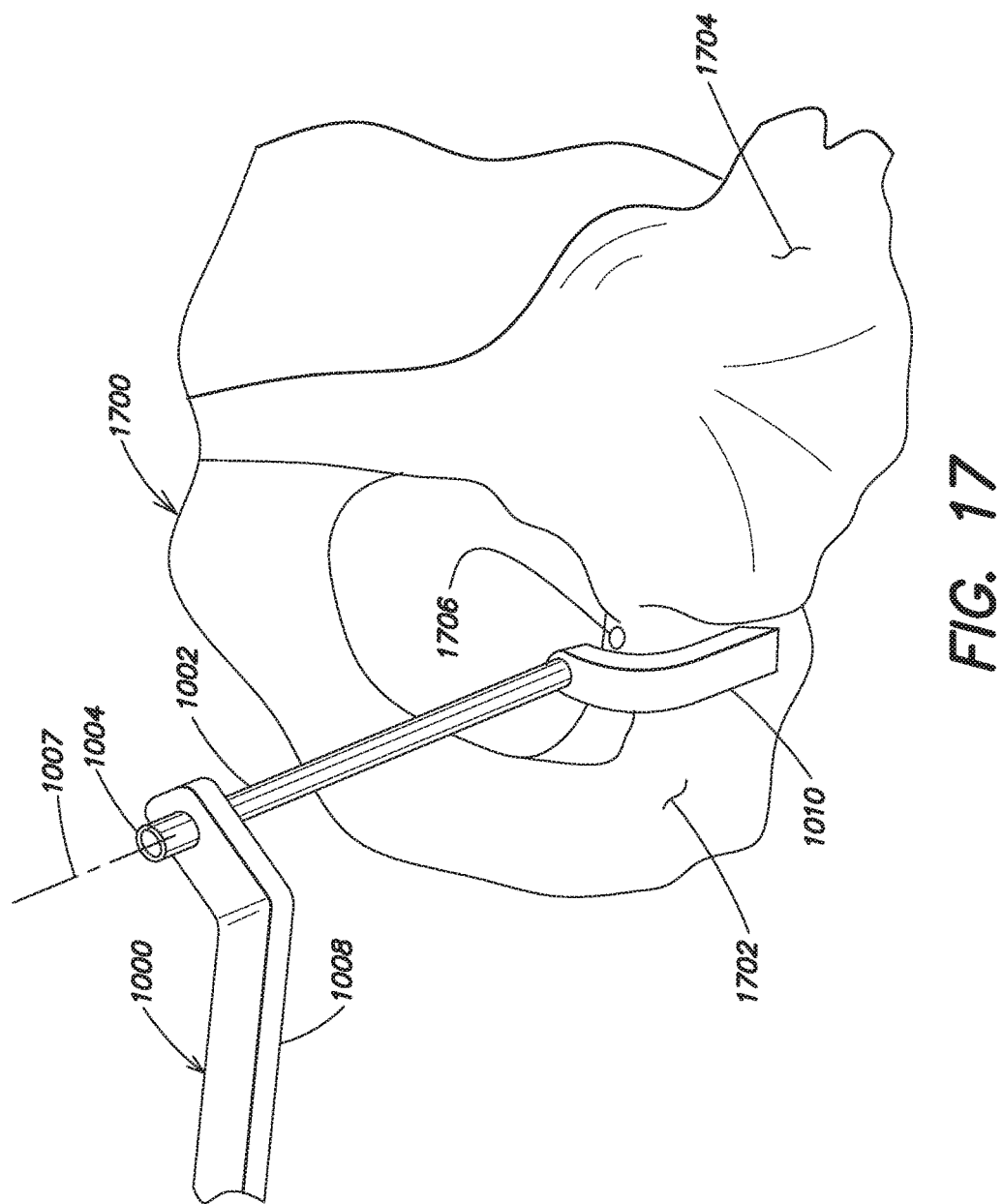
FIG. 17 is a schematic illustration of the drill guide of FIG. 10 on a patient's pelvis.

FIG. 17 is a schematic illustration of the drill guide 1000 being used with a patient's pelvis 1700. The pelvis includes an ischium 1702 and an acetabulum 1704. The finger element 1010 may be positioned at the ischium with the engaging surface 1012 (FIG. 10) in contact with (e.g., held against) the pelvic bone. A surgical drill (not shown) may be fed through the cylindrical tube 1002 of the drill guide, and a hole 1706 may be formed in the patient's pelvis 1700 at the selected basepoint.

A pin may then be placed in this hole 1706, which is located at the selected basepoint. The third leg 108 of the instrument 100 may be hollow, e.g., configured as a cannula, and the instrument 100 may be docked to the patient's pelvis by sliding the third leg 108 over this basepoint pin. A collet may be provided on the third leg 108, and the collet may be tightened to hold the third leg 108 to the pin. Next, the first leg 104 may be docked on the ASIS on the operative side of the patient, e.g., the right ASIS. As the patient is in the supine position on the operating table, the first leg 104, which may include the disc shaped footing, may rest on the skin and tissue over the ASIS. Alternatively, a pin may be placed through the skin and into the ASIS and the first leg 104 also may include a hollow tip that can be slid over this pin and locked, e.g., with a collet. Finally, the second leg 106 may be docked to the ASIS on the non-operating side of the patient. In a similar manner as with the first leg 104, a disc shaped footing of the second leg 106 may rest on the skin and tissue above the opposite side ASIS, or a pin may be inserted into the ASIS, and the third leg, which may be provided with a hollow tip, may be secured to this pin, e.g., by a collet.

The orientation of the direction indicator 160 may be used by the operating surgeon to position and/or align one or more components with respect to the patient's pelvis, as indicated at block 532. For example, the operating surgeon may utilize the direction indicator 160 to fix a component to the patient's pelvis in alignment with the direction indicator 160.

Figure 11:
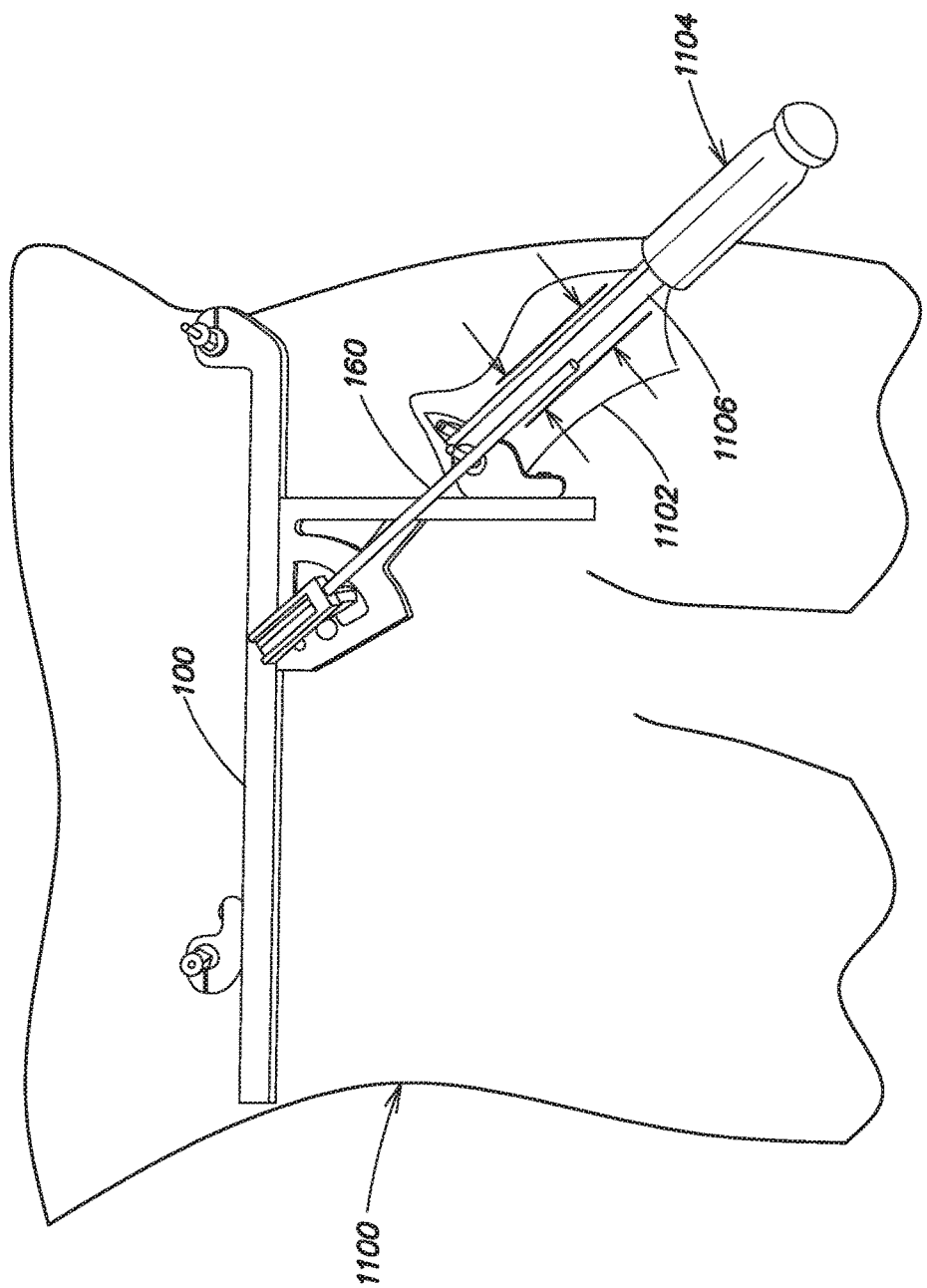
FIG. 11 is a schematic top view of a portion of a patient during the performance of a surgical procedure in accordance with an embodiment of the disclosure.
Figure 12:
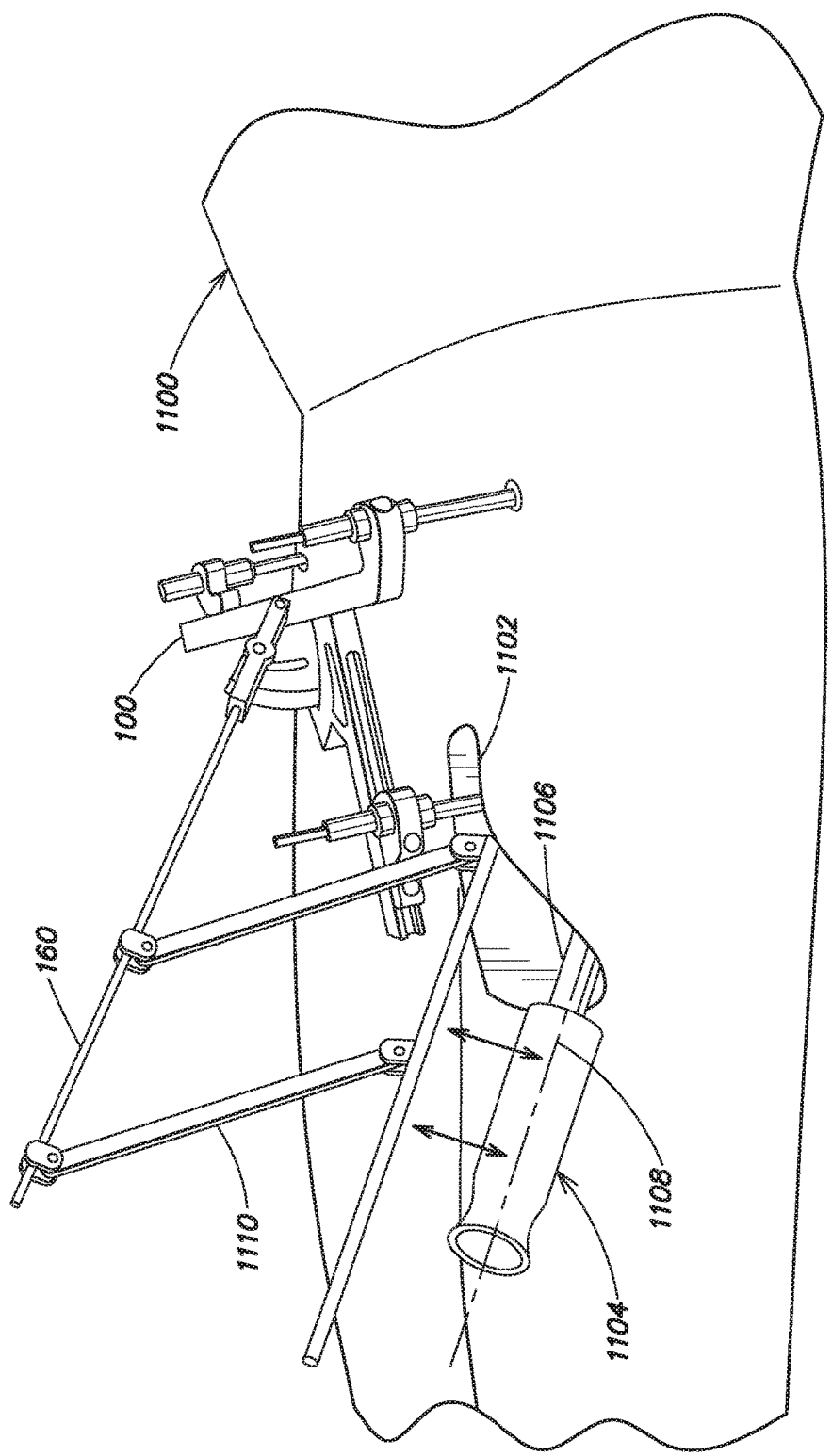
FIG. 12 is a schematic side view of a portion of the patient of FIG. 11 in accordance with an embodiment of the disclosure.

FIG. 11 is a schematic top view of a portion of a patient 1100 during the performance of the surgical procedure. FIG. 12 is a schematic side view of the portion of the patient 1100 of FIG. 11. The patient 1100 may be lying in the supine position on an operating room table. An incision 1102 has been made through the patient's skin and tissue in order to access the patient's left hip. As shown, the surgical instrument 100 is docked to the patient's pelvis. The direction indicator 160 of the surgical instrument 100 has been adjusted per the surgical plan to point along the desired orientation for the acetabular cup component. The surgeon may use a tool, such as a cup inserter tool 1104, to insert the cup component at the desired orientation, which is specified by the direction indicator 160. For example, the cup inserter tool 1104 may have a straight handle portion 1106 defining a central axis 1108 (FIG. 12) that is aligned with, e.g., centered on, the axis of the acetabular cup component. The surgeon may position the handle portion 1106 of the cup inserter tool 1104 (and thus the axis of the cup component) to be aligned with the direction indicator 160. In particular, FIG. 11 illustrates the handle portion 1106 being aligned in a vertical plane with the direction indicator 160, and FIG. 12 illustrates the handle portion 1106 being aligned in a horizontal plane with the direction indicator 160.

In an embodiment, as shown in FIG. 12, one or more other instruments, such as a parallel guide 1110, may be used by the surgeon to translate the orientation defined by the direction indicator 160 to the central axis 1108 of the handle portion 1106 of the cup inserter 1104. A suitable parallel guide is disclosed in U.S. Patent Publication No. 2013/0165941 for a Guide for Acetabular Component Positioning published Jun. 27, 2013, which publication document is hereby incorporated by reference in its entirety.

In an alternative embodiment, the direction indicator 160 and the parallel guide 1110 may be used to insert a pin into the patient's pelvis, e.g., at the acetabulum or another location in the patient's pelvis, that is aligned with the desired orientation for the acetabular cup component. Once the pin is fixed to the patient's pelvis, a guide rod may be attached to the pin, and the surgeon may use this guide rod to set the orientation of the acetabular cup component. Once the acetabular cup component is positioned in the acetabulum at the desired location and in the desired orientation, i.e., as set forth in the surgical plan, the guide rod and pin may be removed.

With the cup component positioned in the patient's acetabulum at the desired location and orientation, the instrument 100 may be removed from the patient 1100, and the surgical procedure may continue. For example, a prosthetic stem having a ball component configured to fit within the acetabular cup component may be attached to the patient's femur.

It should be understood that other or additional steps may be performed during surgical procedure. For example, with the instrument 100 docked or attached to the patient's pelvis, one or more, and preferably three or more (non-collinear), points on the instrument 100 may be digitized using a navigation pointer, also referred to as a digitizing probe, as indicated at block 534. A navigation pointer is a device typically having a tip and a tracker, such as an optical tracker, having a known spatial relationship relative to the tip. The tip of the pointer may be placed on specific points of the instrument 100, and the position within three-dimensional space of the tip, which represents a point, may be captured by a tracking system. The instrument 100 may include mechanical or other features, such as divots, at three or more locations on the instrument 100 for receiving the tip of the pointer. For example, the divots may be located at opposite ends of the elongated support arm 102 and on the guide support frame 110. The divots may be located at points that define a plane and coordinate system that is parallel to the patient-specific, supine pelvic reference plane and coordinate system defined by the tips of the legs 104, 106, and 108 of the instrument 100 when it is docked to the patient. The tracking system may determine the 3D spatial coordinates of these points relative to a coordinate system defined by the tracking system. In this way, the location and orientation, for example the angular orientation, of the patient's pelvis may be registered, relative to the coordinate system defined by the tracking system.

In addition, one or more trackers may be placed on the pelvis. The instrument 100 may then be used to determine the relationship between a given plane such as the AP Plane and the one or more pelvic trackers, which may be randomly affixed to the pelvis. That way, once the instrument is 100 used to register the pelvis, the instrument 100 can be removed and typical navigation sequences can be used, e.g., to place the acetabular cup component at the desired location and/or orientation relative to the patient's pelvis.

In another embodiment, one or more trackers may be attached to the instrument 100. The one or more trackers may be fixedly or removably attached to the instrument 100. For example, a tracker may be permanently mounted to the instrument 100, or a saddle or receptacle may be incorporated into the instrument 100, and a tracker may be removably attached to this saddle or receptacle. Once the tracker is attached or seated to the instrument 100, a tracking system may capture and "memorize" the location of the instrument 100 and its 3D coordinate system relative to one or more other trackers attached to the patient, e.g., to the patient's pelvis. In this way, the patient-specific, supine pelvic reference plane and/or coordinate system may be established relative to the one or more trackers on the patient's pelvis and/or to the AP plane and/or coordinate system.

Using this information, the pelvis may be registered relative to the at least one tracker, because the location of the tracker relative to the patient-specific plane and/or coordinate system can be determined. Furthermore, because the surgical plan may include a translation function between the patient-specific plane and/or coordinate system and the AP plane and/or coordinate system, the relationship between the tracker and the AP plane coordinate system can also be determined. With the patient-specific plane and/or coordinate system captured by the tracking system, the instrument 100 may be removed from the patient.

To provide additional navigation data, for example to more accurately establish a patient-based coordinate system, a plurality of points on the patient's anatomy may also be digitized, i.e., captured by a tracking system. For example, for THR, a plurality of points at and around the patient's acetabulum may be digitized, using the pointer. That is, upon accessing the patient's acetabulum, the surgeon may digitize a plurality of points inside and/or around the acetabulum. These points may be combined with the patient-specific plane and/or coordinate system defined by the instrument 100, when docked to the patient, to establish a coordinate system. More specifically, the tracking system may be configured to compute a center of rotation for the acetabulum based on the plurality of points. The tracking system may set this center of rotation as the origin of the coordinate system. In an embodiment, the surgeon may digitize a large number of points in close proximity to each other to establish the origin. In this embodiment, the instrument 100 may be used primarily to establish the axes of the coordinate system, such as x, y and z axes. That is, the instrument 100 in combination with a plurality of points on the patient's anatomy, such as in the acetabulum, may be used to establish a coordinate system that includes the patient-specific plane and/or coordinate system.

In some cases, a patient's preoperative anatomy may be such that an origin may not be capable of being determined. For example, a patient's acetabulum may be distorted such that a center of rotation cannot be determined. In this case, a cloud of points, for example within and/or outside of the acetabulum, maybe digitized, and a "best fit" matching computation performed, such as a root mean square minimization calculation, that determines how the cloud of captured points may best fit the 3D model surface.

It should be understood that, depending on the procedure being performed, other points on the patient's anatomy may be digitized. Furthermore, points, such as a cloud of points on a bone surface, may be captured by or entered into the tracking system using a tracked ultrasound probe.

In an embodiment, once the patient-specific plane and/or coordinate system is established on the patient, the instrument 100 may be removed, and the surgical procedure may be continued. That is, the instrument 100 may register the location and orientation of the patient in the operating room, and this registration can be tracked by the tracking system through the trackers attached to the patient. The tracking system may track one or more instruments used by the surgeon during the procedure. For example, the tracking system may track one or more instruments manually operated by the surgeon to, e.g., attach one or more prosthetic components, such as the acetabular cup component, to the patient, as specified in the surgical plan.

The tracking system may also be used to track other instruments during the surgical procedure, such as bone preparation instruments. Furthermore, the tracking system may be configured to track changes in leg length, offset, and/or anterior-posterior position. A suitable system for tracking such changes is described in U.S. Pat. No. 7,885,705 for a System and Method for Facilitating Hip Surgery issued Feb. 8, 2011, which patent is hereby incorporated by reference in its entirety.

In yet another embodiment, the instrument 100 may remain docked to the patient during the surgical procedure. In this case, the direction indicator 160 once set, e.g., as set forth in the one or more plans, may be used by the surgeon to attach the one or more prosthetic components at the desired locations and/or orientations.

Figure 14:
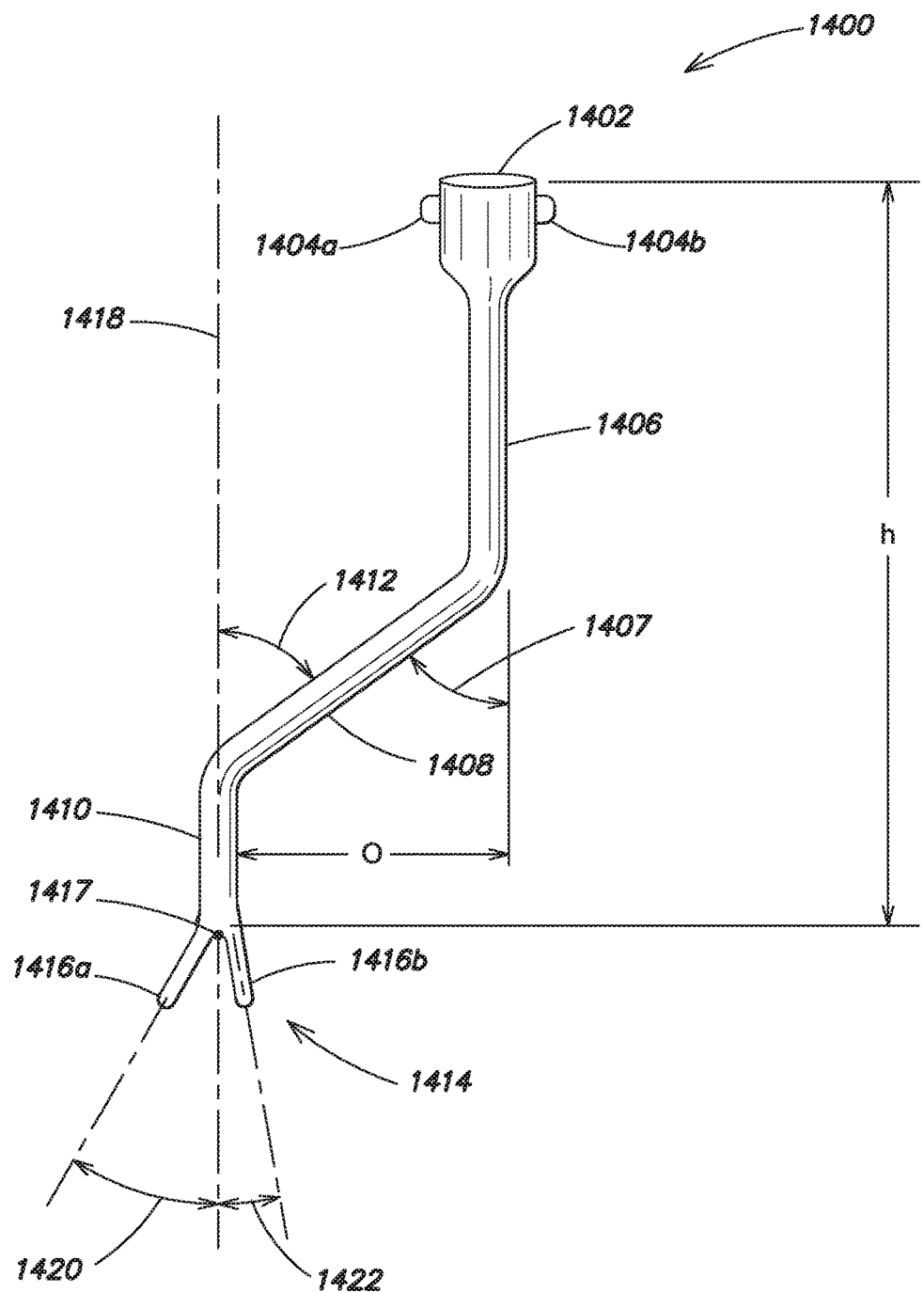
FIG. 14 is a schematic front elevation view of another embodiment of one of the legs of the surgical instrument in accordance with an embodiment of the disclosure.

FIG. 14 is a schematic front elevation view of another embodiment of the third (ischial) leg 1400. The third leg 1400 may include a first end 1402 that is configured to be received in the opening 144 of the first moveable leg brace 114. The first end 1402 may have one or more locking elements, such as locking elements 1404a and 140b. The first moveable leg brace 114 may have a notch 194 (FIG. 2). The locking elements 1404a and 1404b may be spring-loaded and configured so that one of them can be received in the notch 194, thereby securing the third leg 1400 from rotation. As described herein, the instrument 100 may be used on either the right or left hip by flipping the instrument 100 over. By including two locking elements 1404a and 1404b the third leg 1400 may be used on both sides.

The third leg 1400 may include a first straight leg segment 1406 that may extend downwardly directly from the first end 1402, a second straight leg segment 1408 that joins the first straight leg segment 1406 at a first angle 1407, and a third straight leg segment 1410 that joins the second straight leg segment 1406 at a second angle 1412. In an embodiment, the first and second angles may be the same, and may be approximately 45 degrees. The third leg 1400 may further include a second end 1414 that may be V-shaped. That is, the second end 1414 may have first and second arms 1416a and 1416b. The first and second arms 1416a and 1416b are joined at a terminal point 1417 that is the apex of the V-shaped second end 1414. The first arm 1416a may extend from a vertical axis 1418 by a third angle 1420, and the second arm 1416b may extend from the vertical axis 1418 by a fourth angle 1422. The third angle 1420 may be approximately 30 degrees, and the fourth angle 1422 may be approximately 10 degrees. In an embodiment, the third leg 1400 may have an overall height (h) of approximately 140 mm and an offset (width) of approximately 40 mm. In addition, the first and second arms 1416a and 1416b may be approximately 10 mm.

Figure 15:
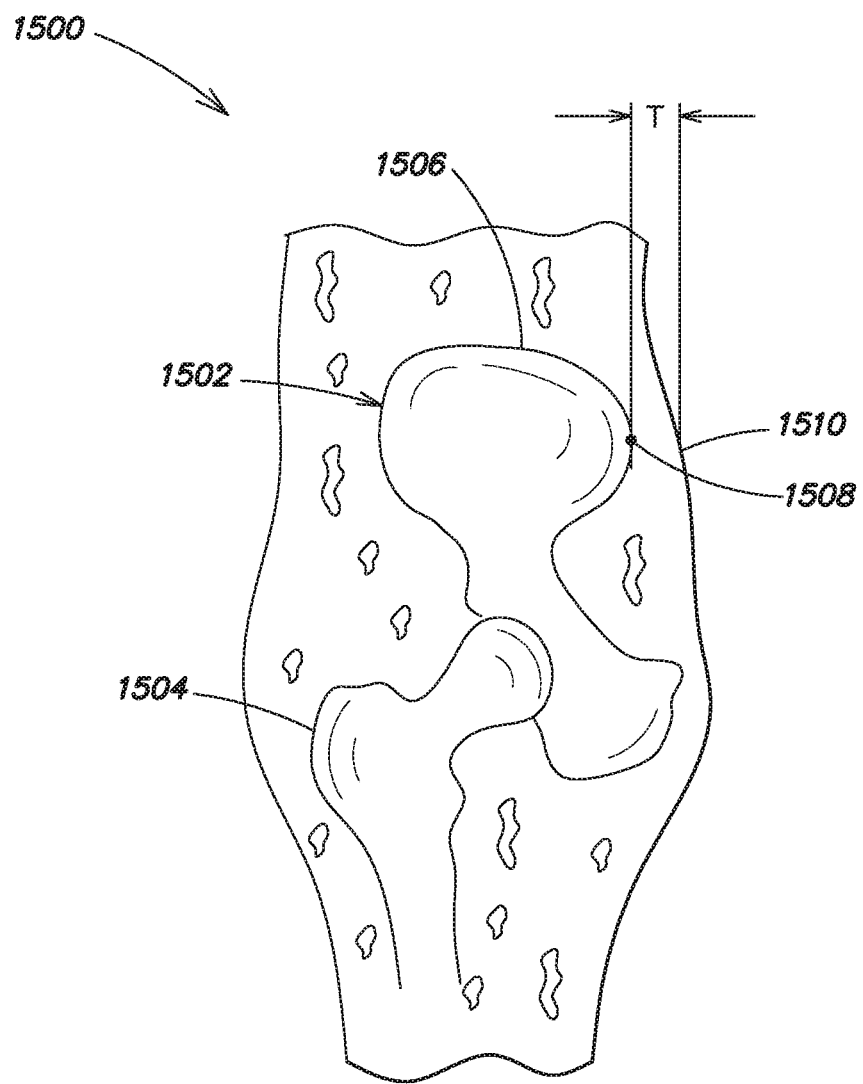
FIG. 15 is a schematic side view of a patient.
Figure 16:
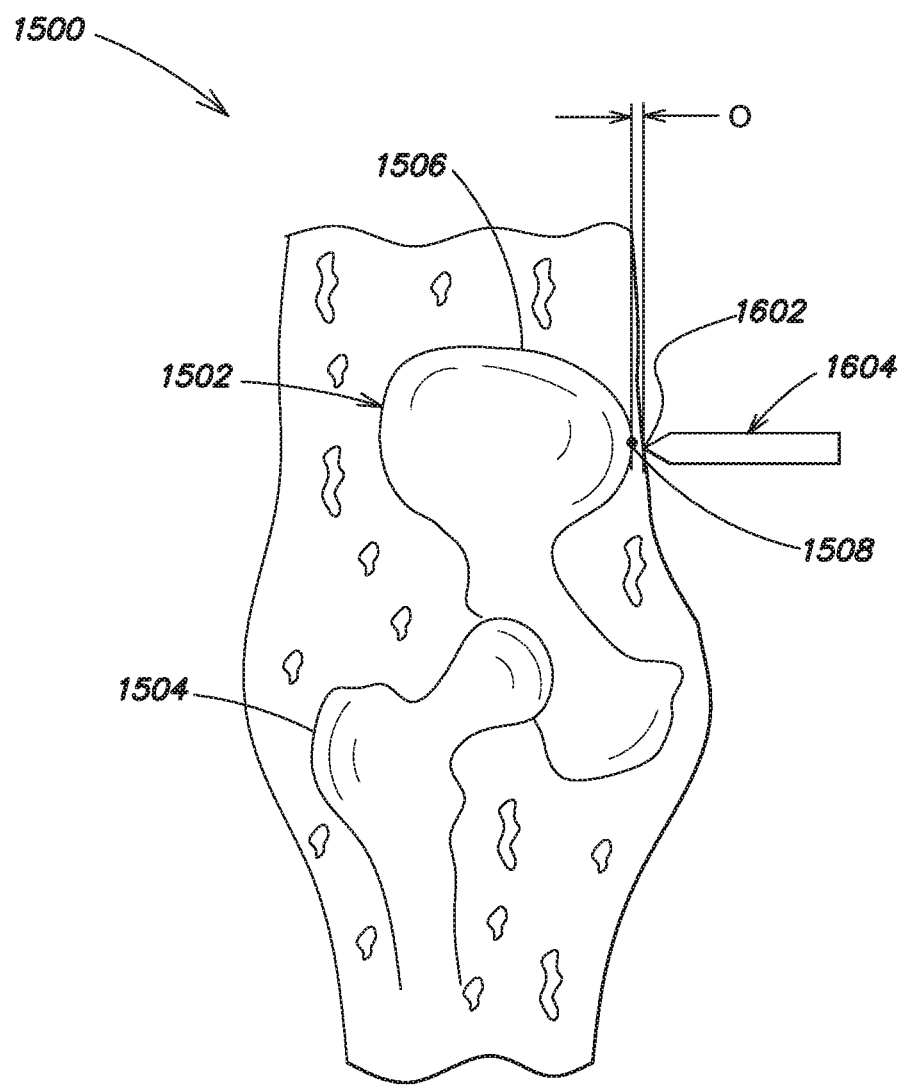
FIG. 16 is a schematic side view of the patient of FIG. 15.

The anterior aspect of the ischium just below the acetabulum typically has a fairly sharp leading edge. Instead of using a drill guide with a 10 mm offset from the lateral or medial side of the ischium, when using a basepoint cannula, the third leg 1400 having the V-shaped second end 1414 may be used. In this case, the V-shaped second end 1414 may be positioned so that the point 1417, which is the apex of the V, is at the sharp leading edge of the ischium with the medial side of the V placed over the medial edge of the ischium and the lateral side of the V placed over the lateral side of the ischium. In an embodiment, the instrument planning module 1306 may be configured to account for the thickness of the patient's skin and tissue at the left and/or right ASIS when determining the patient-specific, supine pelvic reference plane. More specifically, FIG. 15 is a schematic side view of a patient 1500 illustrating the pelvis 1502 and the femur 1504. The pelvis 1502 includes an iliac wing 1506 and right ASIS indicated by a point 1508 on the iliac wing 1506. Around the pelvis 1502 is the patient's skin 1510. Above the right ASIS 1508 is skin and tissue having a thickness or depth indicated by the letter T. FIG. 16 is a schematic side view of the patient 1500 with the tip 1602 of a leg 1604 of the hip registration instrument 100 (FIG. 1) placed at the right ASIS 1508. With the instrument 100 docked to the patient's pelvis 1502, the skin and tissue above the right ASIS 1508 is compressed from its original thickness T (FIG. 15) to a compressed thickness labeled O (FIG. 16). That is, the tip 1602 of the leg 1604 is not quite in contact with the ASIS 1508, but is spaced therefrom by the distance O, which represents is the patient's skin and tissue compressed down against the ASIS 1508 due to the hip registration instrument 100 being placed on the patient.

The instrument planning module 1306 may be configured to add the distance O to the physical length of the leg 1604 to arrive at a "logical" length for the leg 1604. The instrument planning module 1306 may similarly compute a "logical" length for the other leg of the instrument to the extent it too is spaced above the left ASIS by compressed skin and tissue. The distance or thickness of the compressed skin and tissue, O, may be entered into to the planning system 1300, e.g., by the planning surgeon or the operating surgeon, and thus received by the instrument planning module 1306. Alternatively, the instrument planning module 1306 may be configured to estimate the thickness of the compressed skin and tissue based on one or more characteristics of the patient.

Because either or both of the instrument's legs are not in direct contact with the left and/or right ASIS, the nominal plane of the instrument will not be parallel to the patient-specific, supine pelvic reference plane. Nonetheless, because the "virtual" lengths of the instrument's legs are known, the instrument planning module 1306 may still compute the new plane defined by the nominal surface of the instrument 100, and translate the desired acetabular cup component orientation from the AP plane to the patient-specific, pelvic reference plane, and from the patient-specific, pelvic reference plane to this new frame, so that proper settings may be computed for the instrument's direction indicator.

It should be understood that the compressed thickness of skin and tissue, labeled O, may be determined in a number of different ways. In a first embodiment, the compressed thickness may be determined during the planning stage. For example, the instrument planning module 1306 may be configured to determine the thickness of skin and tissue above the two points located at the left and right ASIS based on the received image data, such as the CT studies or images. Based on this determined value, the instrument planning module 1306 may be configured to compute a corresponding compressed thickness value, e.g., based on a mathematical relationship or an algorithm, such as a ratio, a non-linear function, etc., that predicts compressed thickness of skin and tissue based, for example on uncompressed thickness of skin and tissue. The mathematical relationship or algorithm may be derived from empirical data or studies. The mathematical relationship or algorithm may consider other factors besides or in addition to the uncompressed thickness of skin and tissue. In another embodiment, the compressed thickness may be determined during the surgical procedure on the patient. For example, the uncompressed thickness of skin and tissue above the two points located at the left and right ASIS may be measured, e.g., using a calibrated needle placed through the patient's skin and in contact with the two points. The uncompressed thickness may be input to the planning system 1300, which may determine a compressed thickness. In yet another embodiment, the compressed thickness may be directly measured. For example, with the legs 104 and 106 of the hip registration instrument 100 resting on the left and right ASIS above the two respective points, a calibrated needle may be used to measure the thickness of compressed skin and tissue above the respective points. To the extent a surgical drape is present, e.g., above the contralateral ASIS, its thickness may also be included. The measured compressed values may be entered into the surgical planner 1300, which may utilize the received values to determine logical leg lengths and thus the new plane and coordinate system of the instrument 100.

In addition, the compressed thickness of skin and tissue may be determined on one side of the pelvis, e.g., the left ASIS, and that value may be used on the other side, e.g., the right ASIS.

In an embodiment, the instrument 100 is configured for easy use on either the right or left hip. FIG. 2 illustrates the instrument 100 as set up for surgery on the patient's right hip. In this embodiment, the first leg 104, which is fixed, e.g., not moveable, relative to the elongated support arm 102 is docked to the patient's right ASIS, as described herein.

In order to use the instrument 100 on a patient's left hip, the guide support frame 110 and the first moveable leg brace 114 may be removed from the elongated support arm 102, and the elongated support arm 102 may be flipped over so that the bottom surface 128 is now facing up, as shown in FIGS. 1 and 3. The guide support frame 110 and the first moveable leg brace 114 may then be slid along the first and second tracks 134, 136 to the pre-operatively determined locations for the specific patient, as is done when the instrument 100 is used on the patient's right hip.

In another embodiment, one or more of the legs may be fixedly attached to the instrument, rather than being removably attached. For example, the first, second and/or third leg may be fixedly attached to the elongated support arm (either directly or indirectly).

The foregoing description of embodiments is intended to provide illustration and description, but is not intended to be exhaustive or to limit the invention to the precise form disclosed. Modifications and variations are possible in light of the above teachings or may be acquired from a practice of the invention. For example, while a series of acts has been described above, the order of the acts may be modified in other implementations. Further, non-dependent acts may be performed in parallel. Also, the term "user", as used herein, is intended to be broadly interpreted to include, for example, a computer or data processing system or a user of a computer or data processing system, unless otherwise stated.

Further, certain embodiments of the invention may be implemented as logic that performs one or more functions. This logic may be hardware-based, software-based, or a combination of hardware-based and software-based. Some or all of the logic may be stored in one or more tangible non-transitory computer-readable storage media and may include computer-executable instructions that may be executed by a computer or data processing system, such as a server system. The computer-executable instructions may include instructions that implement one or more embodiments of the invention. The tangible non-transitory computer-readable storage media may be volatile or non-volatile and may include, for example, flash memories, dynamic memories, removable disks, and non-removable disks.

As shown, with the instrument 100, the basepoint may be at the root of the anterior ischium and is thus within the incision and thus within the surgical field. Accordingly, the basepoint of the instrument 100 represents a reliable basepoint. This basepoint also represents a significant improvement over the use of the pubic symphysis as a possible third reference point. For example, the pubic symphysis can be difficult to palpate. In addition, there are vital structures nearby the pubic symphysis. With the instrument 100, there is no need to palpate or otherwise contact the pubic symphysis.

What is claimed is:

1. An apparatus for establishing a supine pelvic reference plane for a specific patient, the apparatus comprising:
   an elongated support arm;
   a first leg attached to the elongated support arm;
   a second leg slidably attached to the elongated support arm, wherein the second leg slides along the elongated support arm; and
   a third leg slidably attached to the elongated support arm, wherein the third leg slides along the elongated support arm, and wherein;
   the first, second, and third legs have tips,
   the first leg is closer to one end of the elongated support arm than the second leg and the third leg; and
   the second and third legs are slidably adjusted relative to the elongated support arm such that:
     the tip of the first leg is configured to contact a left anterior superior iliac spine of the specific patient,
     the tip of the second leg is configured to contact a right anterior superior iliac spine of the specific patient, and
     the tip of the third leg is configured to contact an anterior aspect of an ischium of a pelvis of the specific patient below an acetabulum, and further wherein
   the apparatus defines the supine pelvic reference plane for the specific patient, and
   the supine pelvic reference plane has a known relationship to a standard reference plane for the specific patient.

2. The apparatus of claim 1 further comprising:
   a directional indicator attached to the elongated support arm, the directional indicator defining a predetermined orientation relative to the apparatus.

3. The apparatus of claim 2 wherein the elongated support arm defines a nominal plane, and the predetermined orientation is relative to the nominal plane defined by the elongated support arm.

4. The apparatus of claim 1 further comprising:
   a platform slidably attached to the elongated support arm, wherein the third leg is attached to the platform.

5. The apparatus of claim 4 wherein the third leg is slidably attached to the platform such that the third leg is moveable in a direction orthogonal to a longitudinal axis of the elongated support arm.

6. The apparatus of claim 5 further comprising:
   a directional indicator mounted to the platform, the directional indicator defining a predetermined orientation relative to the apparatus.

7. The apparatus of claim 6 wherein the elongated support arm defines a nominal plane, and the directional indicator is fixedly adjustable in
a first direction that is within the nominal plane defined by the elongated support arm, and
a second direction that is normal to the nominal plane defined by the elongated support arm.

8. The apparatus of claim 7 wherein the directional indicator is pivotable in the first and second directions.

9. The apparatus of claim 1 wherein
the first, second, and third legs are releasably attached to the elongated support arm, and
the elongated support arm is reversible for use on a left hip and a right hip of the specific patient.

10. The apparatus of claim 1 wherein the elongated support arm defines a nominal plane, and the nominal plane defined by the elongated support arm is parallel to a plane defined by:
the left anterior superior iliac spine of the specific patient;
the right anterior superior iliac spine of the specific patient; and
the anterior aspect of the ischium of the pelvis of the specific patient below the acetabulum.

11. The apparatus of claim 10 wherein the first, second, and third legs have equal lengths.

12. A method comprising:
defining a standard pelvic plane for a patient;
defining a supine pelvic reference plane for the patient;
establishing a mathematical relationship between the standard pelvic plane and the supine pelvic reference plane;
determining an orientation for a prosthetic component relative to the standard pelvic plane;
translating the orientation to the supine pelvic reference plane;
docking a registration device to predetermined points on a pelvis of the patient; and
providing a directional indicator on the registration device, where the directional indicator is configured to define the orientation for the prosthetic component.

13. The method of claim 12 wherein the standard pelvic plane is an anterior pelvic (AP) plane.

14. The method of claim 12 wherein the supine pelvic reference plane includes:
a first point at a left anterior superior iliac spine of the patient;
a second point at a right anterior superior iliac spine of the patient; and
a third point at an anterior aspect of an ischium of a pelvis of the patient below an acetabulum.

15. The method of claim 14 wherein
the registration device has first, second, and third legs that terminate in respective tips,
the predetermined points include:
the left anterior superior iliac spine of the patient;
the right anterior superior iliac spine of the patient; and
the anterior aspect of the ischium of the pelvis of the patient below the acetabulum, and
the tips of the first, second, and third legs of the registration device contact or are proximate to the predetermined points.

16. The method of claim 15 wherein the registration device includes an elongated support arm, and the second and third legs are slidable along the elongated support arm, the method further comprising:
determining locations along the elongated support arm for the second and third legs; and
adjusting the second and third legs along the elongated support arm to the determined locations.

17. The method of claim 12 wherein the prosthetic component is an acetabular cup component.

18. The method of claim 12 further comprising:
utilizing a three-dimensional computer model to define the standard pelvic plane and the supine pelvic reference plane.

19. The method of claim 18 further comprising:
obtaining one or more images of the pelvis of the patient; and
generating the three-dimensional computer model of the pelvis of the patient from the one or more images.

20. A surgical registration device comprising:
a support bar having
first and second ends,
a longitudinal axis, and
a nominal plane;
a first leg removably attached proximate to the first end of the support bar;
a second leg removably and adjustably attached proximate to the second end of the support bar, where the second leg is adjustable in a direction along the longitudinal axis;
a third leg removably and adjustably attached to the support bar, where the third leg is adjustable in a first direction along the longitudinal axis and in a second direction orthogonal to the longitudinal axis; and
a direction indicator mounted to the support bar, the direction indicator defining a predetermined orientation relative to the nominal plane of the support bar.

21. An apparatus comprising:
an elongated support arm having a length, the length of the elongated support arm defining an axis;
a first leg attached proximate to an end of the elongated support arm;
a second leg slidably attached to the elongated support arm in a direction along the axis defined by the length of the elongated support arm;
a platform slidably attached to the elongated support arm in the direction along the axis defined by the length of the elongated support arm;
a third leg slidably attached to the platform in a direction orthogonal to the axis defined by the length of the elongated support arm; and
a directional indicator attached to the elongated support arm;
wherein
the elongated support arm defines a nominal plane,
the first leg, the second leg, and the third leg extend from the nominal plane defined by the elongated support arm, and
the directional indicator defines a predetermined orientation in space relative to the nominal plane defined by the elongated support arm.

22. The apparatus of claim 21 wherein a first tip of the first leg is configured to contact a left anterior superior iliac spine of a patient, a second tip of the second leg is configured to contact a right anterior superior iliac spine of the patient, and a third tip of the third leg is configured to contact an anterior aspect of an ischium of a pelvis of the patient below an acetabulum.

23. The apparatus of claim 21 wherein the apparatus defines a supine pelvic reference plane for a patient.

24. The apparatus of claim 23 wherein the supine pelvic reference plane has a known relationship to a standard reference plane for the patient.

25. The apparatus of claim 21 wherein the directional indicator is fixedly adjustable in a first direction that is within the nominal plane defined by the elongated support arm, and a second direction that is normal to the nominal plane defined by the elongated support arm.

26. The apparatus of claim 25 wherein the directional indicator is pivotable in the first and second directions.

27. The apparatus of claim 21 wherein
the first leg, the second leg, and the platform are releasably attached to the elongated support arm, and
the elongated support arm is reversible for use on a left hip and a right hip of a patient.

28. The apparatus of claim 21 wherein the nominal plane defined by the elongated support arm is parallel to a plane defined by a first tip of the first leg, a second tip of the second leg, and a third tip of the third leg.

29. The apparatus of claim 21 wherein the first, second, and third legs have equal lengths.

30. A method for establishing a supine pelvic reference plane for a patient, the method comprising:
providing an apparatus, the apparatus including:
a support bar having
a first end, a second end, and a length,
a longitudinal axis defined by the length of the support bar, and
a nominal plane;
a first leg removably attached to the first end of the support bar;
a second leg removably and adjustably attached to the second end of the support bar, wherein the second leg is adjustable in a first direction along the longitudinal axis;
a third leg removably and adjustably attached to the support bar, wherein the third leg is adjustable in the first direction along the longitudinal axis and in a second direction orthogonal to the longitudinal axis; and
a direction indicator mounted to the support bar, wherein the first, second, and third legs extend from the support bar and have tips;
configuring the tip of the first leg of the apparatus to contact a left anterior superior iliac spine of the patient;
configuring the tip of the second leg to contact a right anterior superior iliac spine of the patient;
configuring the tip of the third leg to contact an anterior aspect of an ischium of a pelvis of the patient below an acetabulum; and
adjusting the direction indicator of the apparatus to define a predetermined orientation relative to the nominal plane defined by the support bar of the apparatus.

31. The method of claim 30 wherein the apparatus defines the supine pelvic reference plane for the patient.

32. The method of claim 31 wherein the supine pelvic reference plane has a known relationship to a standard reference plane for the patient.

33. The method of claim 30 wherein the directional indicator is fixedly adjustable in a first direction that is within the nominal plane of the support bar, and a second direction that is normal to the nominal plane of the support bar.

34. The method of claim 33 wherein the directional indicator is pivotable in the first and second directions.

35. The method of claim 30 wherein
the first leg, the second leg, and the third leg are releasably attached to the support bar, and
the support bar is reversible for use on a left hip and a right hip of the patient.

36. The method of claim 30 wherein the nominal plane of the support bar is parallel to a plane defined by the tip of the first leg, the tip of the second leg, and the tip of the third leg.

37. The method of claim 30 wherein the first, second, and third legs have equal lengths.

\* \* \* \* \*